United States Patent
Dumićet al.

(10) Patent No.: US 6,936,591 B2
(45) Date of Patent: Aug. 30, 2005

(54) AMORPHOUS 9-DEOXO-9A-AZA-9A-METHYL-9A-HOMOERYTHROMYCIN A, PROCESS FOR PREPARING THE SAME, AND USES THEREOF

(75) Inventors: Miljenko Dumić, Zagreb (HR); Mladen Vinković, Čakovec (HR); Marina Oresic, Sesvete (HR); Ernest Mestrovic, Bjelovar (HR); Aleksandar Danilovski, Rijeka (HR); Alojz Dumbovic, Zagreb (HR); Knezevic Zdravka, Zagreb (HR); Gorjana Lazarevski, Zagreb (HR); Darko Filic, Zagreb (HR); Dominik Cincic, Zagreb (HR); Katica Lazaric, Zagreb (HR); Dejan-Kresimir Bucar, Pušća (HR)

(73) Assignee: Pliva Pharmaceutical Industry, Incorporated, Zagreb (HR)

( * ) Notice: Subject to any disclaimer, the term of this patent is extended or adjusted under 35 U.S.C. 154(b) by 0 days.

(21) Appl. No.: 10/624,911

(22) Filed: Jul. 21, 2003

(65) Prior Publication Data

US 2004/0092460 A1 May 13, 2004

(30) Foreign Application Priority Data

Jul. 22, 2002 (HR) ..................... P 20020614 A

(51) Int. Cl.[7] .......................... A61K 31/70; C07H 1/00; C07H 17/08
(52) U.S. Cl. .......................... 514/29; 536/7.4; 536/18.5; 536/127
(58) Field of Search .............................. 514/29; 536/7.4, 536/18.5, 127

(56) References Cited

U.S. PATENT DOCUMENTS

| | | | |
|---|---|---|---|
| 4,517,359 A | 5/1985 | Kobrehel et al. | |
| 5,869,629 A | 2/1999 | Bayod Jasanda et al. | |
| 6,245,903 B1 | * 6/2001 | Karimian et al. | ............ 536/7.4 |

(Continued)

FOREIGN PATENT DOCUMENTS

| | | |
|---|---|---|
| EP | 0298650 A2 | 2/1992 |
| EP | 0827965 A2 | 3/1998 |
| EP | 0984020 A3 | 3/2000 |
| EP | 1103558 A2 | 5/2001 |
| WO | WO 94 26758 | 11/1994 |
| WO | WO 99 58541 | 11/1999 |
| WO | WO 00 32203 | 6/2000 |
| WO | WO 01 00640 A1 | 1/2001 |
| WO | WO 01 49697 A1 | 7/2001 |
| WO | WO 01 87912 A1 | 11/2001 |
| WO | WO 02 09640 A2 | 2/2002 |
| WO | WO 02 10144 A1 | 2/2002 |
| WO | WO 02 15842 A2 | 2/2002 |
| WO | WO 02 42315 | 5/2002 |
| WO | WO 02 085898 | 10/2002 |
| WO | WO 02/087596 A2 | 11/2002 |
| WO | WO 02 094843 A1 | 11/2002 |
| WO | WO 03 063838 | 8/2003 |
| WO | WO 03 077830 | 9/2003 |
| WO | WO 03 082889 | 10/2003 |
| WO | WO 03 102009 | 12/2003 |

OTHER PUBLICATIONS

Ognjen Čulić et al., Anti–inflammatory effects of macrolide antibiotics, European Journal of Pharmacology 429:209–229 (2001).

(Continued)

Primary Examiner—Elli Peselev
(74) Attorney, Agent, or Firm—Darby & Darby

(57) ABSTRACT

Substantially pure amorphous 9-deoxo-9a-aza-9a-methyl-9a-homoerythromycin A. In addition, this disclosure is directed to a process for the preparation thereof from crude 9-deoxo-9a-aza-9a-methyl-9a-homoerythromycin A via orthorhombic isostructural pseudopolymorphs of 9-deoxo-9a-aza-9a-methyl-9a-homoerythromycin A, of the general formula I:

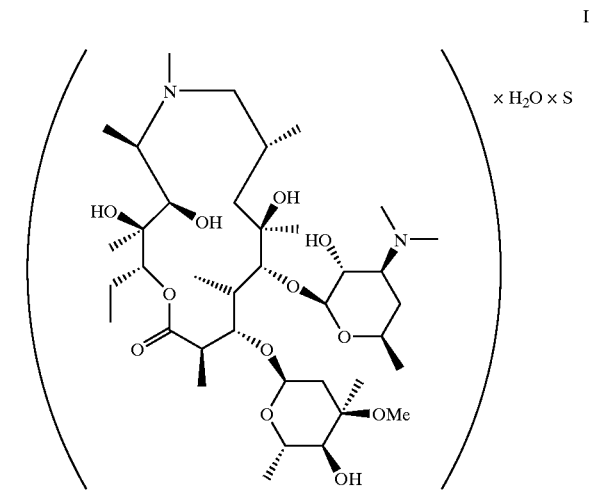

wherein S represents a water-miscible or water-immiscible organic solvent, characterized by the orthorhombic space group $P2_12_12_1$, with average unit cell parameters a=8.2 to 9.7 Å, b=11.5 to 13.5 Å, c=44.5 to 47.0 Å, $\alpha=\beta=\gamma=90°$, wherein a, b and c represent the crystal axes lengths and $\alpha$, $\beta$ and $\gamma$ represent the angles between the crystal axes.

In addition, pharmaceutical compositions containing the substantially pure amorphous 9-deoxo-9a-aza-9a-methyl-9a-homoerythromycin A are disclosed, as well as a method for the treatment of bacterial and protozoal infections, and inflammation related diseases in humans and animals by administration of a pharmaceutical composition containing same.

33 Claims, 9 Drawing Sheets

U.S. PATENT DOCUMENTS

| | | |
|---|---|---|
| 6,268,489 B1 | 7/2001 | Allen et al. |
| 6,365,574 B2 | 4/2002 | Singer et al. |
| 6,420,537 B1 | 7/2002 | Bosch et al. |
| 6,451,990 B1 | 9/2002 | Bayod Jasanada et al. |
| 6,528,492 B1 | 3/2003 | de la Torre Garcia et al. |
| 6,586,576 B2 | 7/2003 | Aronhime et al. |
| 2001/0047089 A1 | 11/2001 | Aronhime et al. |
| 2003/0139583 A1 | 7/2003 | Singh et al. |
| 2003/0162730 A1 | 8/2003 | Li et al. |
| 2003/0165563 A1 | 9/2003 | Murphy et al |
| 2003/0190365 A1 | 10/2003 | Fergione et al. |

OTHER PUBLICATIONS

Ognjen Čulić et al., Azithromycin modulates neutrophil function and circulating inflammatory mediators in healthy human subjects, European Journal of Pharmaclogy 450:277–289 (2002).

F. Scaglione and G. Rossoni, Comparative anti–inflammatory effects of roxithromycin, azithromycin and clarithromycin, Journal of Antimicrobial Chemotherapy 41, Suppl. B, 47–50 (1998).

M.T. Labro, Anti–inflammatory activity of macrolides: a new therapeutic potential? Journal of Antimicrobial Chemotherapy 41, Suppl. B, 37–46 (1998).

* cited by examiner

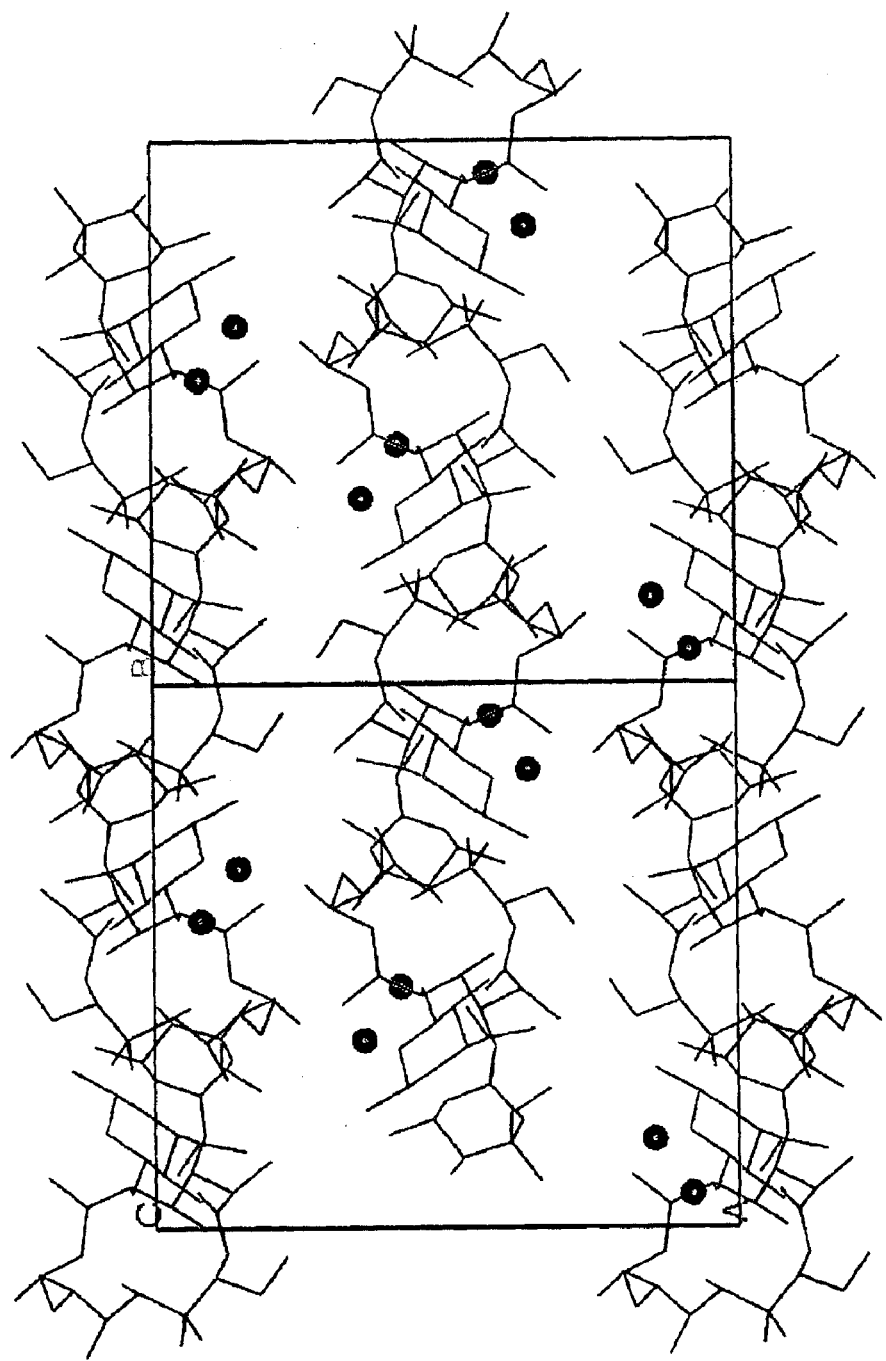
Fig. 1 Crystal packing of 9-deoxo-9a-aza-9a-methyl-9a-homoerythromycin A dihydrate (the structure is disclosed in Cambridge Structural Database under the code GEGJAD).

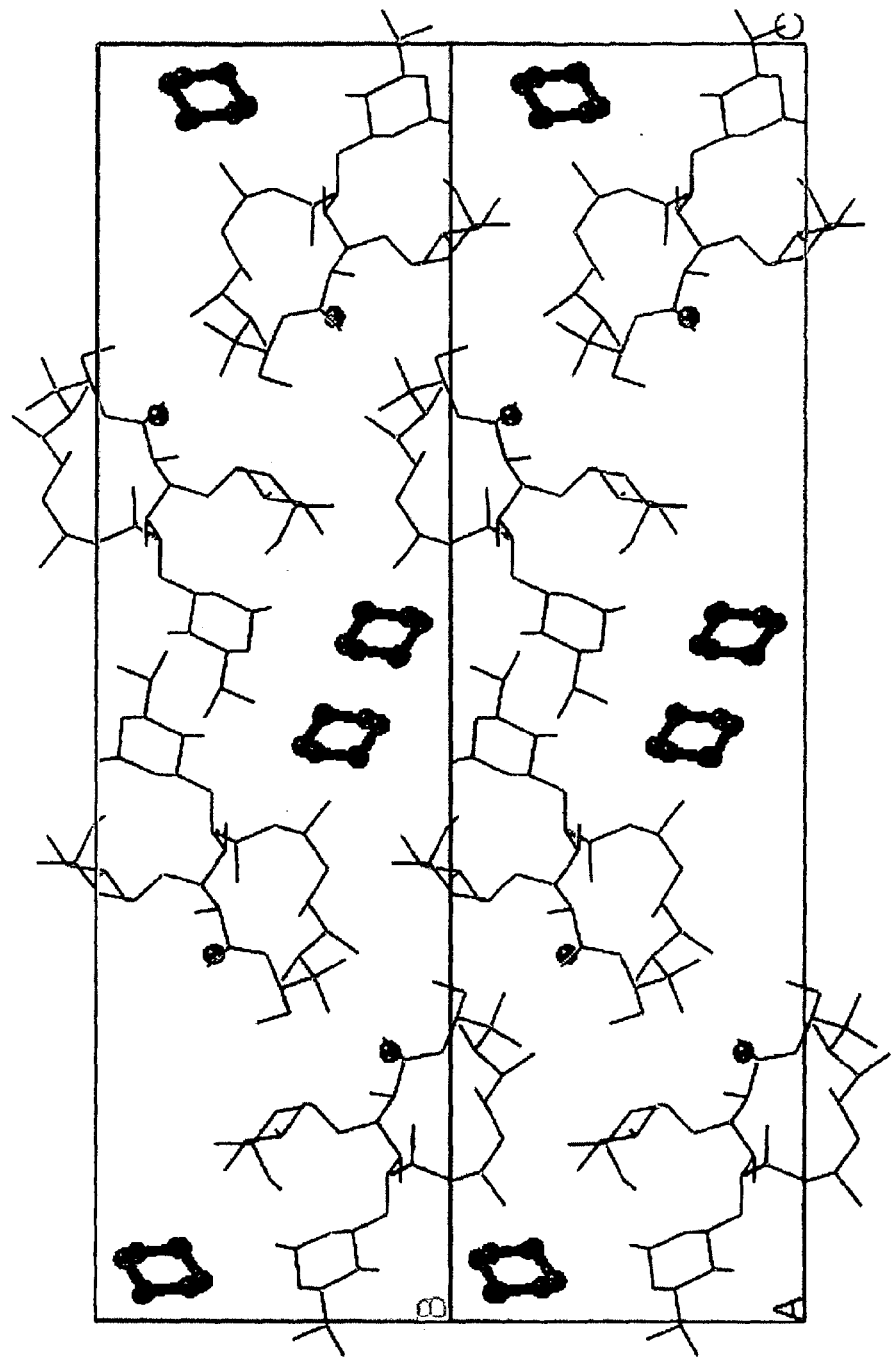
Fig. 2 Crystal packing of a novel orthorhombic isostructural pseudopolymorph of 9-deoxo-9a-aza-9a-methyl-9a-homoerythromycin A of the general formula I (Ia: S = 1,4-dioxane).

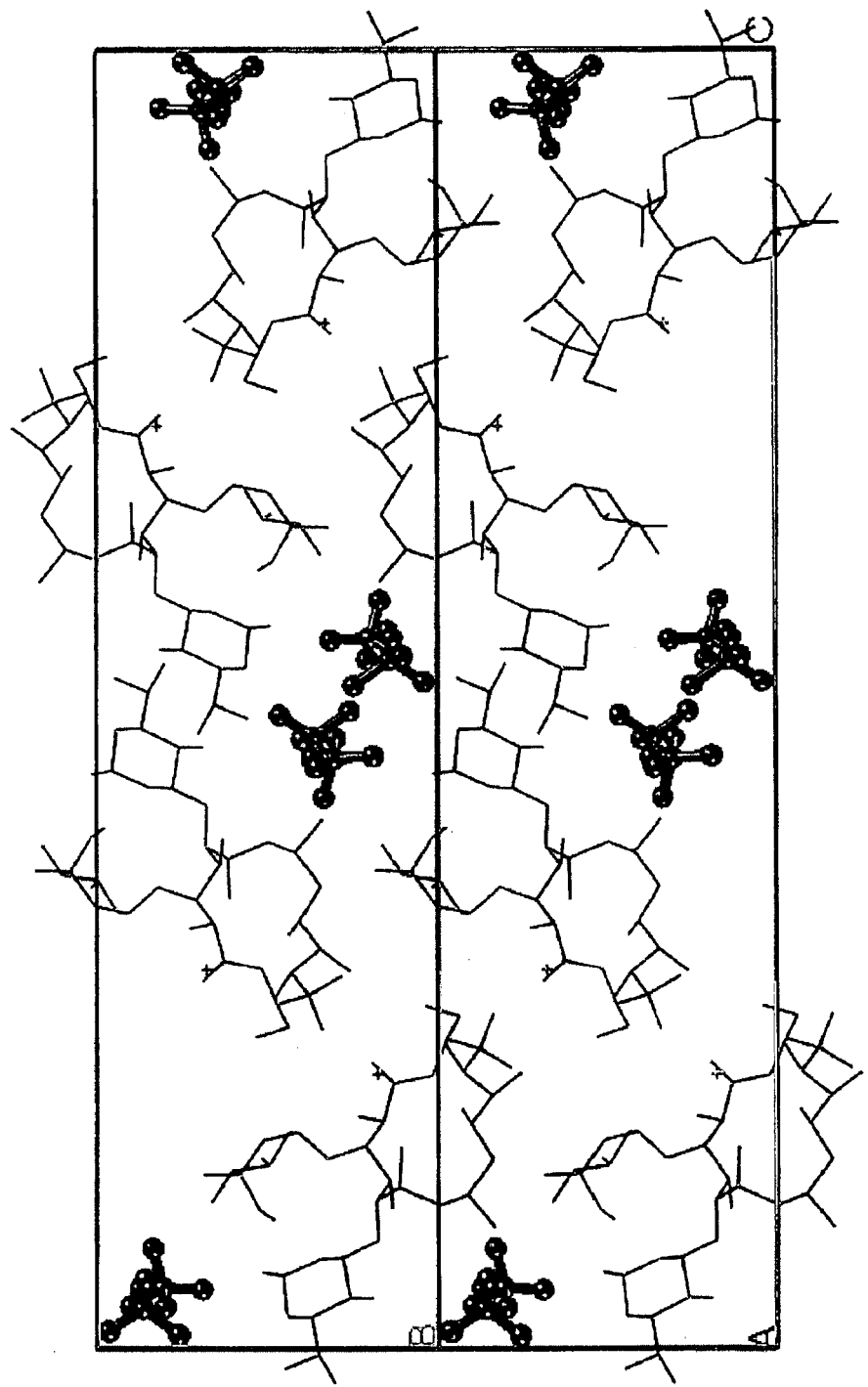
Fig. 3 Crystal packing of a novel orthorhombic isostructural pseudopolymorph of 9-deoxo-9a-aza-9a-methyl-9a-homoerythromycin A of the general formula I (Ib: S = *tert*-butanol).

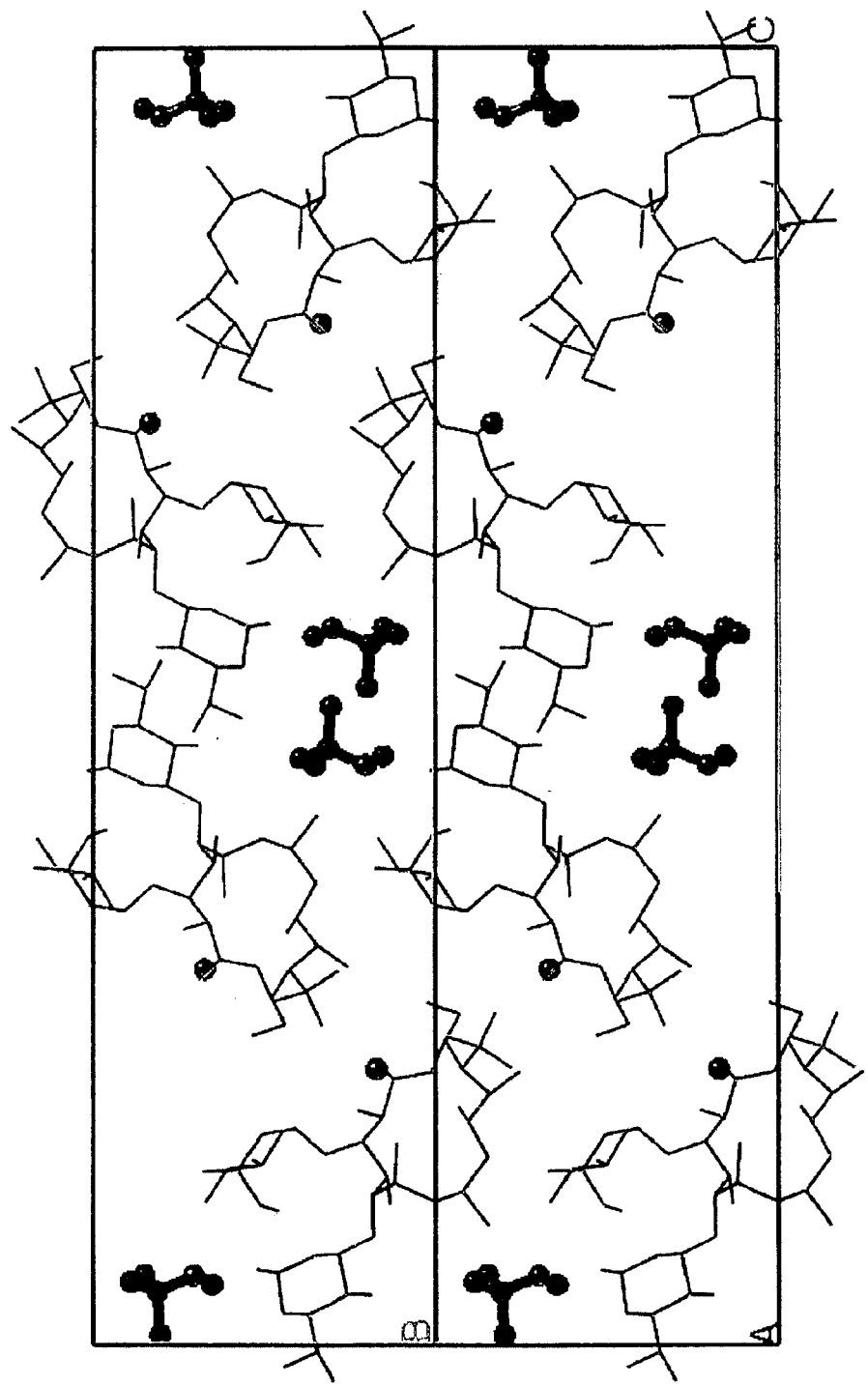
Fig. 4 Crystal packing of a novel orthorhombic isostructural pseudopolymorph of 9-deoxo-9a-aza-9a-methyl-9a-homoerythromycin A of the general formula I (Ic: S = methyl *tert*-butyl ether).

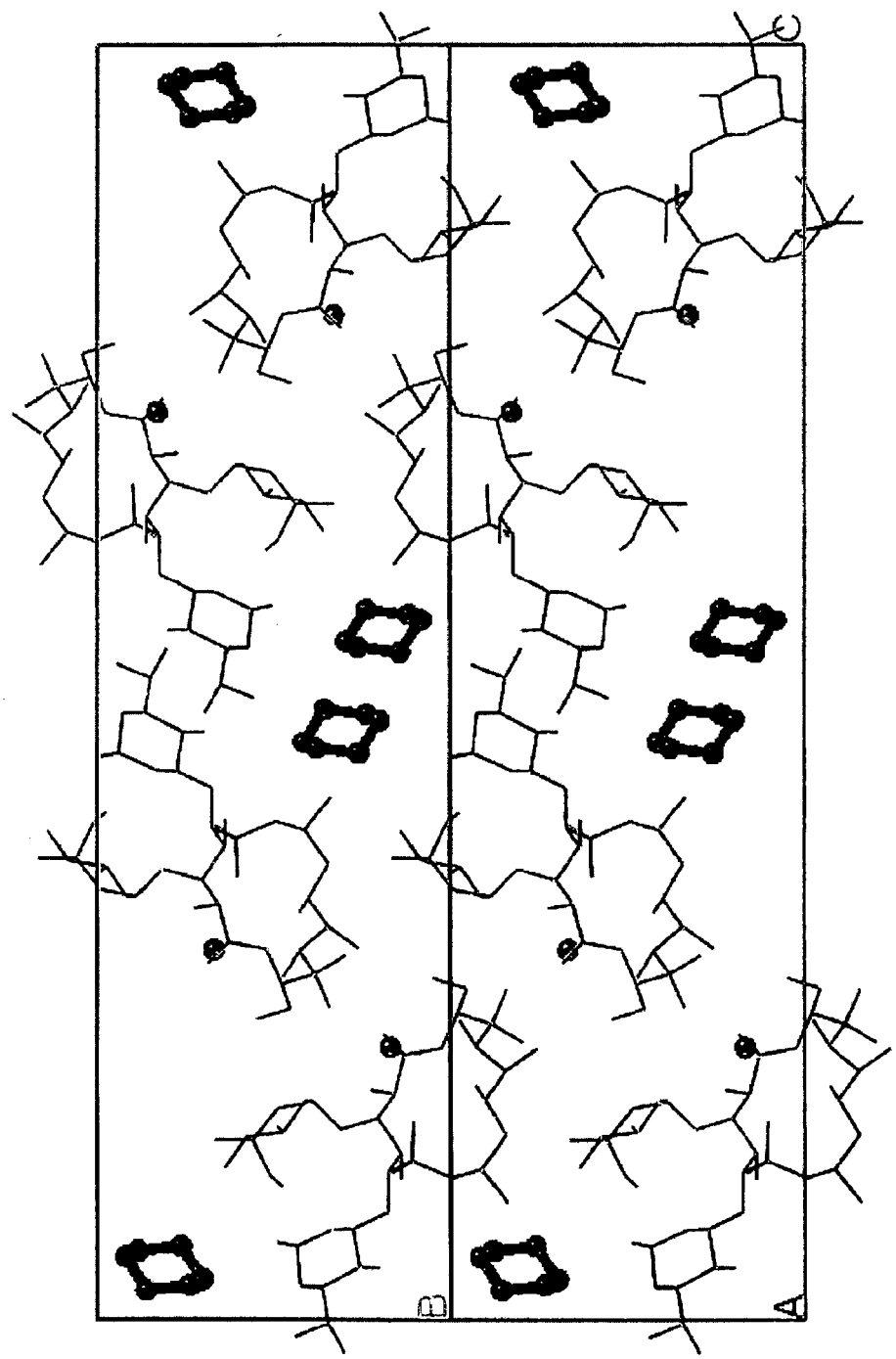
Fig. 5 Crystal packing of a novel orthorhombic isostructural pseudopolymorph of 9-deoxo-9a-aza-9a-methyl-9a-homoerythromycin A of the general formula I (Id: S = cyclohexane).

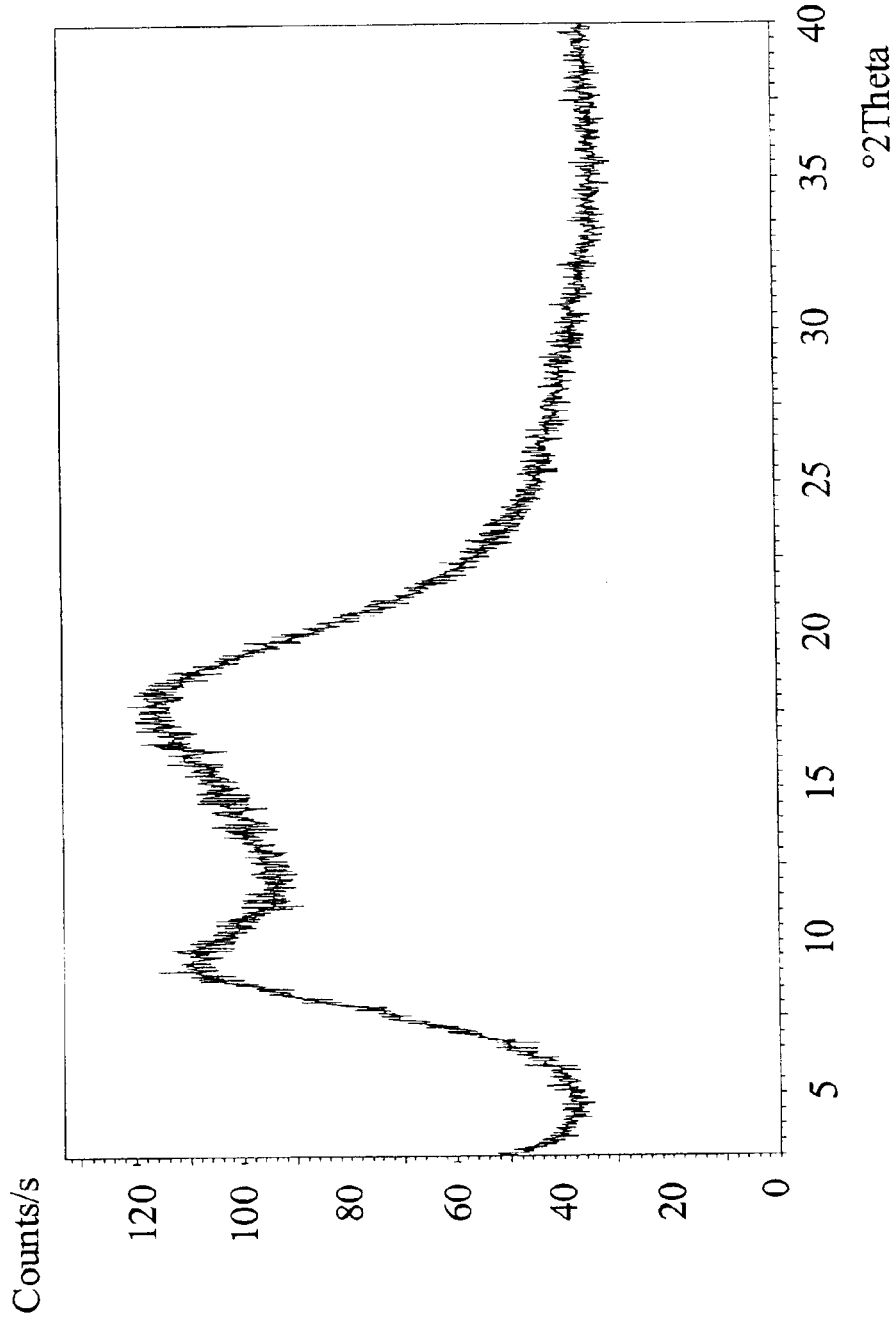
Fig. 6 Powder diffractogram of a novel amorphous 9-deoxo-9a-aza-9a-methyl-9a-homoerythromycin A, prepared according to the process of Example 11.

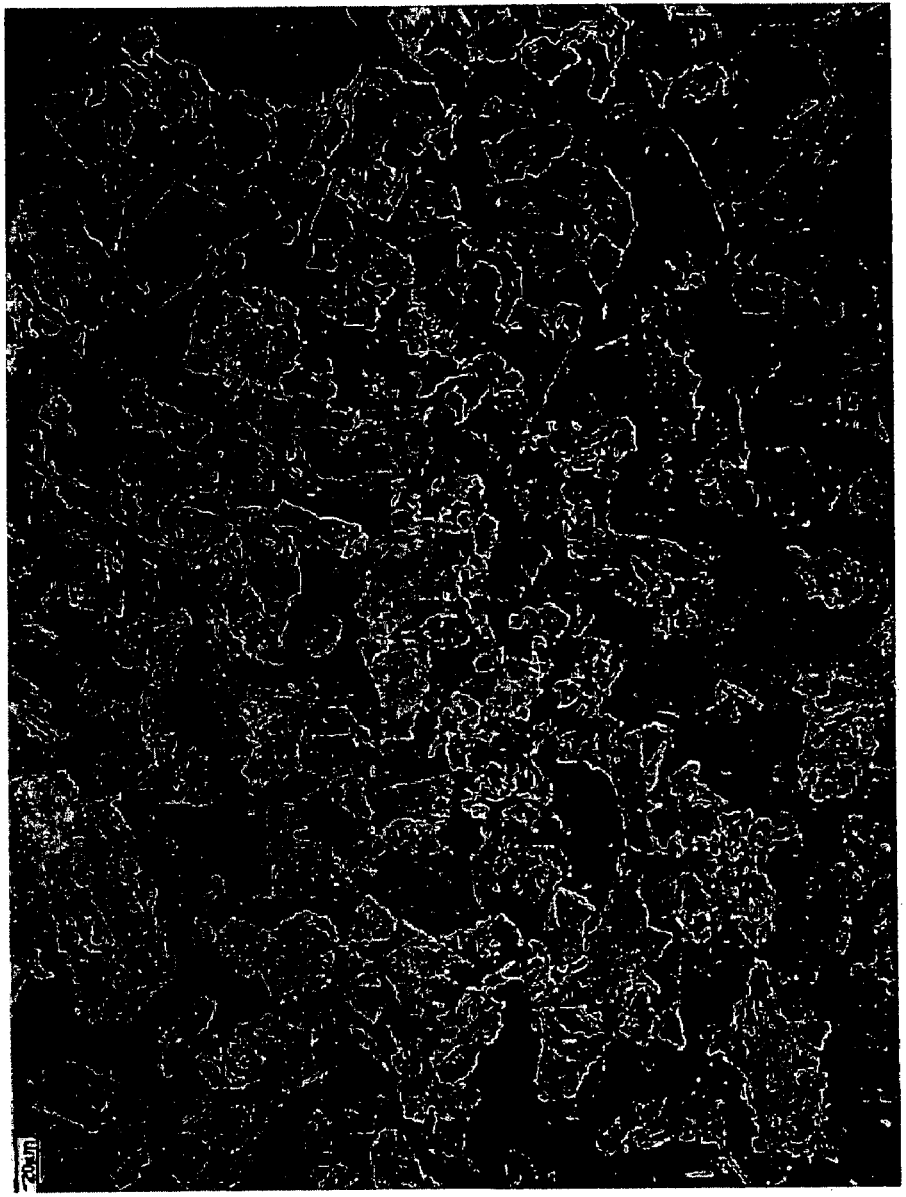
Fig. 7 SEM of the surface of the new amorphous 9-deoxo-9a-aza-9a-methyl-9a-homoenthromycin A prepared according to Example 11.

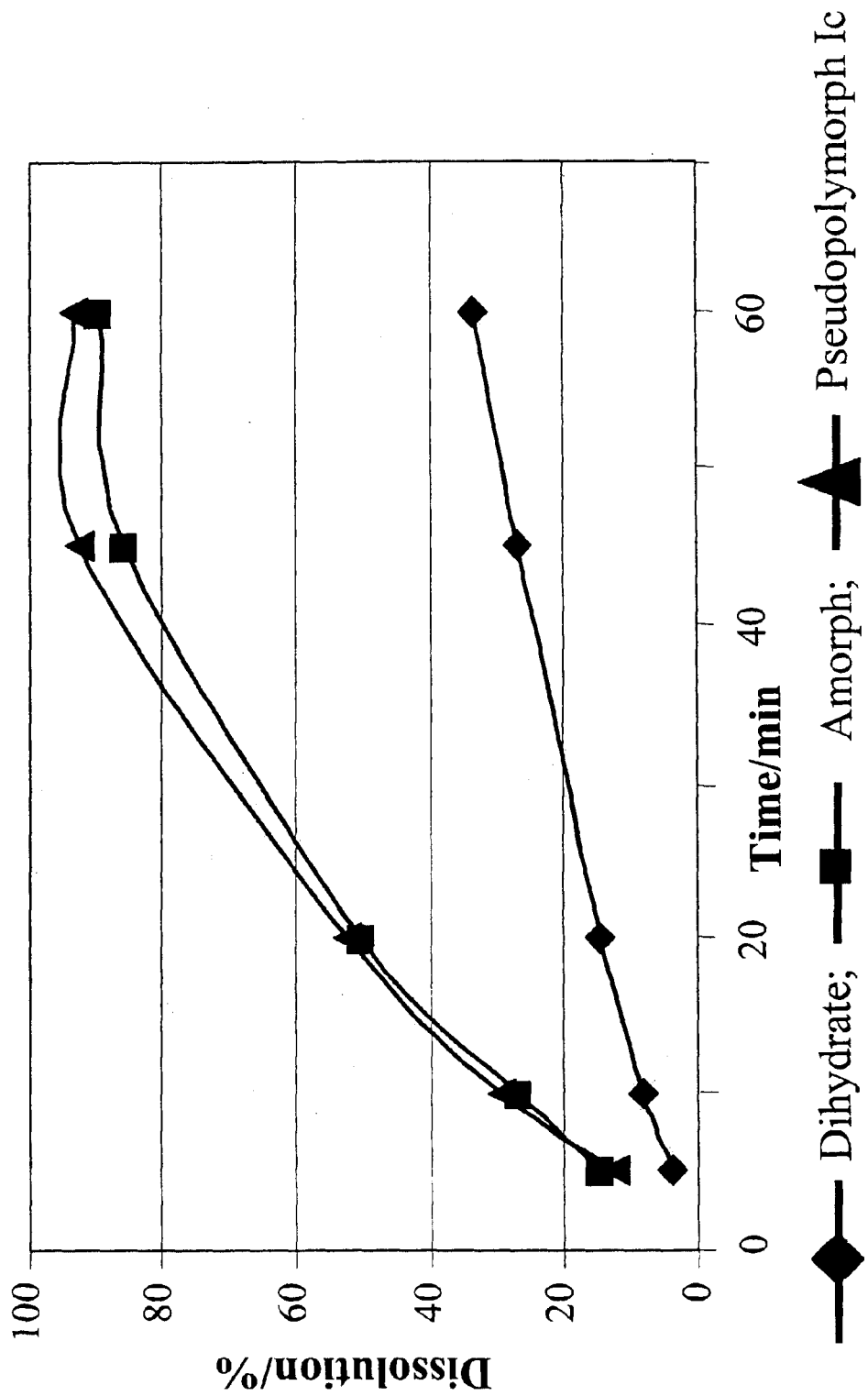
Figure 8: Dissolution rates of a new amorphous 9-deoxo-9a-aza-9a-methyl-9a-homoerithromycin A (Example 11), new isostructural orthorhombic pseudopolymorph of 9-deoxo-9a-aza-9a-methyl-9a-homoerithromycin A of general formula I (Ic: S = MTBE) (Example 3), and commercial 9-deoxo-9a-aza-9a-methyl-9a-homoerithromycin A dihydrate in the medium pH 3 at 37 °C.

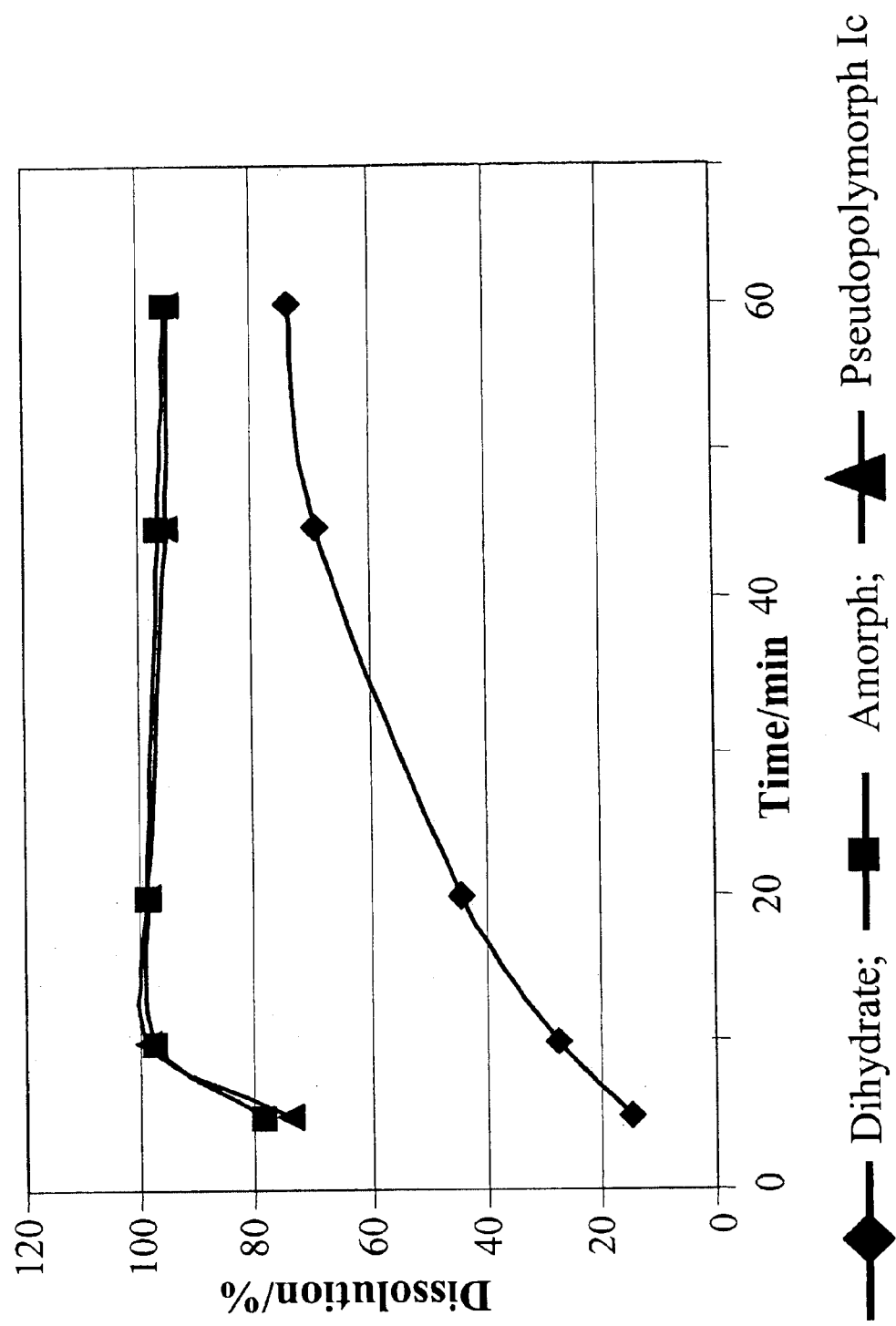
Figure 9: Dissolution rates of a new amorphous 9-deoxo-9a-aza-9a-methyl-9a-homoerithromycin A (Example 11), new isostructural orthorhombic pseudopolymorph of 9-deoxo-9a-aza-9a-methyl-9a-homoerithromycin A of general formula I (Ic: S = MTBE) (Example 3), and commercial 9-deoxo-9a-aza-9a-methyl-9a-homoerithromycin A dihydrate in the medium pH 6 at 37 °C.

AMORPHOUS 9-DEOXO-9A-AZA-9A-METHYL-9A-HOMOERYTHROMYCIN A, PROCESS FOR PREPARING THE SAME, AND USES THEREOF

This application claims the benefit of Croatian Patent Application No. P20020614A, filed Jul. 22, 2002, which is hereby incorporated by reference.

FIELD OF THE INVENTION

The invention relates to a new, substantially pure amorphous 9-deoxo-9a-aza-9a-methyl-9a-homoerythromycin A, to a process for the preparation thereof via new orthorhombic isostructural pseudopolymorphs of 9-deoxo-9a-aza-9a-methyl-9a-homoerythromycin A as intermediates, to pharmaceutical formulations incorporating amorphous 9-deoxo-9a-aza-9a-methyl-9a-homoerythromycin A and/or the orthorhombic isostructural pseudopolymorphs of 9-deoxo-9a-aza-9a-methyl-9a-homoerythromycin A, and to methods of use of such formulations for the treatment of bacterial and protozoan infections, and inflammation-related diseases.

BACKGROUND OF THE INVENTION 9-deoxo-9a-aza-9a-methyl-9a-homoerythromycin A is the first and still the only marketed 15-membered semi-synthetic macrolide antibiotic from the group of azalides [The Merck Index, 12$^{th}$ Ed. (1996), p. 157 (946)]. It has the formula

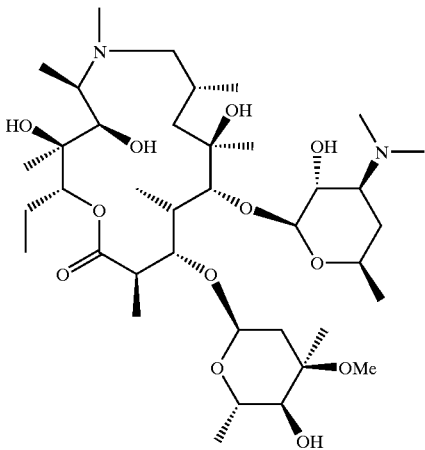

The synthesis of 9-deoxo-9a-aza-9a-methyl-9a-homoerythromycin A is described in U.S. Pat. No. 4,517,359. Its antibacterial spectrum (J. Antimicrob. Chemother., 1987, 19, 275), mode of action (Antimicrob. Ag. Chemother., 1987, 31, 1939) and pharmacology (J. Antimicrob. Chemother. 1993, 31, Suppl. E, 1–198) are well known.

9-deoxo-9a-aza-9a-methyl-9a-homoerythromycin A occurs in amorphous form, and in several different crystal forms characterized by different arrangements of the atoms in the crystal network. Most of the forms are crystalline, their crystal unit cells containing, in addition to 9-deoxo-9a-aza-9a-methyl-9a-homoerythromycin A, different numbers of water molecules and/or solvent molecules (pseudopolymorphs).

Anhydrous amorphous 9-deoxo-9a-aza-9a-methyl-9a-homoerythromycin A, having a melting point of 113–115° C., is described in U.S. Pat. No. 4,517,359. It may be obtained by evaporation of the solvent from a chloroform solution of crude 9-deoxo-9a-aza-9a-methyl-9a-homoerythromycin A. It is not crystalline but rather an amorphous product, resembling a solid foaming mass. A pure laboratory scale product may be obtained, either by chromatography of the crude final product or by dissolution of pure crystalline 9-deoxo-9a-aza-9a-methyl-9a-homoerythromycin A monohydrate or dihydrate in an organic solvent, followed by evaporation of the solvent. Pure amorphous anhydrous 9-deoxo-9a-aza-9a-methyl-9a-homoerythromycin A may be thus obtained. This procedure is not suitable for large-scale manufacture.

The preparation of various amorphous, crystalline solvated and hydrated forms of 9-deoxo-9a-aza-9a-methyl-9a-homoerythromycin A has been described in the patent literature. See, for example, U.S. Pat. No. 4,474,768; U.S. Pat. No. 6,245,903; EP 1 103 558; CN 1 093370; CN 1 161971; WO 99/58541; WO 00/32203; WO 01/00640; WO 02/09640; WO 02/10144; WO 02/15842; WO 02/10181 and WO 02/42315. Materials so produced have been subject to various disadvantages including lack of purity, instability, hygroscopicity, and the like. Non-hygroscopic 9-deoxo-9a-aza-9a-methyl-9a-homoerythromycin A dihydrate was prepared as early as the mid-1980's by neutralization of an acidic solution of 9-deoxo-9a-aza-9a-methyl-9a-homoerythromycin A in an acetone-water mixture. Its crystal structure (single crystal) was evaluated upon recrystallization from ether, and was characterized by the orthorhombic space group P $2_1 2_1 2_1$. The unit cell parameters, namely crystal axes a=17.860 Å, b=16.889 Å and c=14.752 Å, and the angles between the crystal axes, $\alpha=\beta=\gamma=90°$, were published in 1987 at the Meeting of Chemists of Croatia (Book of Abstracts, Meeting of Chemists of Croatia, Feb. 19–20, 1987, p. 29). Thereafter, its crystal structure and preparation were described in detail (J. Chem. Res. (S), 1988, 152, Ibid., miniprint 1988, 1239; received Jun. 4, 1987; Cambridge Crystallographic Data Base: GEGJAD).

Subsequently, in U.S. Pat. No. 6,268,489 9-deoxo-9a-aza-9a-methyl-9a-homoerythromycin A dihydrate was described. That patent disclosed the preparation of the dihydrate by crystallization from tetrahydrofuran and hexane with the addition of water. The product thus formed is crystalline and can be obtained on a commercial scale in pure form. Its preparation is however subject to several disadvantages associated with the use of water-immiscible, toxic organic solvents and the necessity to carefully control the drying thereof.

Other techniques for preparing the dihydrate have been disclosed in the patent literature, e.g., in U.S. Pat. No. 5,869,629; EP 0 941 999; EP 1 103 558; HR P 921491; WO 01/49697; and WO 01/87912. Various of the procedures described involve the precipitation of the dihydrate by recrystallization from water-miscible solvents by the addition of water. The products formed by these and other processes described in the literature are however subject to a number of distinct disadvantages, ranging from the necessity to treat pharmaceutically pure 9-deoxo-9a-aza-9a-methyl-9a-homoerythromycin A materials to the yield, purity and homogeneity of the products themselves. Indeed, products formed by various of the prior art techniques incorporate differing amounts of combined and adsorbed solvents and water, thus imparting inconsistent stability, purity, release and potency characteristics when incorporated in pharmaceutical formulations.

In HR patent application No. P20020231A monoclinic isostructural pseudopolymorphs of 9-deoxo-9a-aza-9a-methyl-9a-homoerythromycin A are disclosed.

Now it has been surprisingly found out that a substantially pure amorphous 9-deoxo-9a-aza-9a-methyl-9a-homoerythromycin A may also be prepared from crude 9-deoxo-9a-aza-9a-methyl-9a-homoerythromycin A without using chromatography techniques, via new orthorhombic isostructural pseudopolymorphs of 9-deoxo-9a-aza-9a-methyl-9a-homoerythromycin A intermediates.

SUMMARY OF THE INVENTION

The invention relates to a new process for the preparation of substantially pure amorphous 9-deoxo-9a-aza-9a-methyl-9a-homoerythromycin A from crude 9-deoxo-9a-aza-9a-methyl-9a-homoerythromycin A via new orthorhombic isostructural pseudopolymorphs of 9-deoxo-9a-aza-9a-methyl-9a-homoerythromycin A as intermediates, comprising the steps of:

a) dissolving 9-deoxo-9a-aza-9a-methyl-9a-homoerythromycin A material in
  (1) an organic solvent that is water-miscible or water-immiscible,
  (2) a mixture of such organic solvents,
  (3) a mixture of organic solvents and water or organic counter-solvent, or
  (4) a mixture of organic solvent and water and at least one inorganic or organic acid;

b) crystallizing a new orthorhombic isostructural pseudopolymorph of 9-deoxo-9a-aza-9a-methyl-9a-homoerythromycin A of the general Formula I

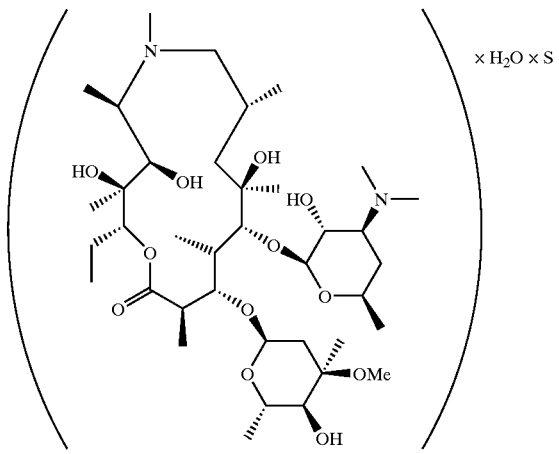

I wherein S is a water-miscible or water-immiscible organic solvent,
the pseudopolymorphs being characterized by the orthorhombic space group $P2_12_12_1$, and average unit cell parameters of:
crystal axis lengths from a=8.2 to 9.7 Å, b=11.5 to 13.5 Å, c=44.5 to 47.0 Å, and
angles between the crystal axes of $\alpha=\beta=\gamma=90°$;

c) isolating the new orthorhombic isostructural pseudopolymorph of 9-deoxo-9a-aza-9a-methyl-9a-homoerythromycin A of the general formula I; and d) converting the new orthorhombic isostructural pseudopolymorph of 9-deoxo-9a-aza-9a-methyl-9a-homoerythromycin A of the general Formula I to substantially pure amorphous 9-deoxo-9a-aza-9a-methyl-9a-homoerythromycin A.

Further, the invention also relates to new orthorhombic isostructural pseudopolymorphs of 9-deoxo-9a-aza-9a-methyl-9a-homoerythromycin A of the general Formula I:

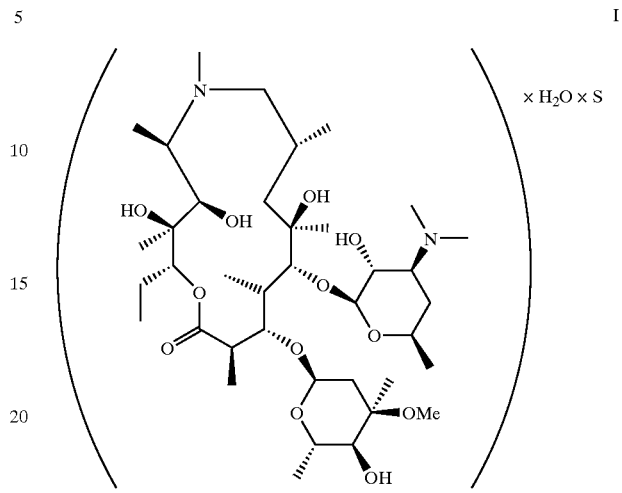

I wherein S is a water-miscible or water-immiscible organic solvent;
the pseudopolymorphs being characterized by the orthorhombic space group $P2_12_12_1$, and average unit cell parameters of;
crystal axis lengths from a=8.2 to 9.7 Å, b=11.5 to 13.5 Å, c=44.5 to 47.0 Å, and
angles between the crystal axes of $\alpha=\beta=\gamma=90°$. These new orthorhombic isostructural pseudopolymorphs of 9-deoxo-9a-aza-9a-methyl-9a-homoerythromycin A of the general Formula I are useful as intermediates in preparing the substantially pure amorphous 9-deoxo-9a-aza-9a-methyl-9a-homoerythromycin A, as well as active ingredients in pharmaceutical mixtures and formulations.

Further, the invention relates to a new, substantially pure stable amorphous 9-deoxo-9a-aza-9a-methyl-9a-homoerythromycin A.

The invention also relates to pharmaceutical mixtures containing (a) a new, substantially pure, amorphous 9-deoxo-9a-aza-9a-methyl-9a-homoerythromycin A and/or the new orthorhombic isostructural pseudopolymorphs of 9-deoxo-9a-aza-9a-methyl-9a-homoerythromycin A of the general Formula I, and (b) pharmaceutically acceptable excipients.

The invention also relates to pharmaceutical formulations containing a substantially pure amorphous 9-deoxo-9a-aza-9a-methyl-9a-homoerythromycin A and/or the orthorhombic isostructural pseudopolymorphs of 9-deoxo-9a-aza-9a-methyl-9a-homoerythromycin A of the general Formula I as the active substance.

The invention also relates to a method for the treatment of bacterial and protozoal infections and inflammation-related diseases in humans and animals subject thereto involving the administration of such pharmaceutical formulations to subjects in need of such treatment.

In accordance with the preferred invention, the substantially pure amorphous 9-deoxo-9a-aza-9a-methyl-9a-homoerythromycin A and the process for its preparation via new orthorhombic pseudopolymorphs show numerous advantages over existing forms of 9-deoxo-9a-aza-9a- methyl-9a-homoerythromycin A and processes used for the preparation thereof.

The substantially pure amorphous 9-deoxo-9a-aza-9a-methyl-9a-homoerythromycin A prepared in accordance with the invention, may, unlike the present dihydrate, be reproducibly prepared under a wide range of preparative conditions.

Second, it can be prepared directly from the native solution of crude 9-deoxo-9a-aza-9a-methyl-9a-homoerythromycin A or from the crude 9-deoxo-9a-aza-9a-methyl-9a-homoerythromycin A itself, rather than from any purified 9-deoxo-9a-aza-9a-methyl-9a-homoerythromycin A material. The number of preparation steps is thereby reduced, the process is simplified, and the overall yield is increased.

Third, the new substantially pure amorphous 9-deoxo-9a-aza-9a-methyl-9a-homoerythromycin A may be prepared in the present process in high purity and pharmaceutically acceptable quality.

Fourth, the new substantially pure amorphous 9-deoxo-9a-aza-9a-methyl-9a-homoerythromycin A is a granular product, and has a free-flowing form.

Fifth, the substantially pure amorphous 9-deoxo-9a-aza-9a-methyl-9a-homoerythromycin A is stable under normal storage conditions.

Sixth, the substantially pure amorphous 9-deoxo-9a-aza-9a-methyl-9a-homoerythromycin A (as well as the orthorhombic isostructural pseudopolymorphs of 9-deoxo-9a-aza-9a-methyl-9a-homoerythromycin A of the general Formula I) has a significantly better (improved) specific dissolution rate as compared with the dihydrate.

Seventh, the intrinsic dissolution rate (IDR) of the substantially pure amorphous 9-deoxo-9a-aza-9a-methyl-9a-homoerythromycin A is significantly higher than the dissolution rate of the dihydrate.

Eighth, the substantially pure amorphous 9-deoxo-9a-aza-9a-methyl-9a-homoerythromycin A, may be used in the preparation of a variety of pharmaceutical preparations posssessing an excellent stability profile intended for immediate, controlled or sustained release applications.

Ninth, because of its superior dissolution characteristics, the stable substantially pure amorphous 9-deoxo-9a-aza-9a-methyl-9a-homoerythromycin A, unlike other forms of 9-deoxo-9a-aza-9a-methyl-9a-homoerythromycin A, can be successfully utilized in the preparation of rapidly acting oral and local, particularly locally active transdermal, formulations.

BRIEF DESCRIPTION OF THE DRAWINGS

FIG. 1 is a crystal packing diagram of a 9-deoxo-9a-aza-9a-methyl-9a-homoerythromycin A dihydrate (the structure coded GEGJAD described in the Cambridge Structural Database).

FIG. 2 is a crystal packing diagram of an orthorhombic isostructural pseudopolymorph of 9-deoxo-9a-aza-9a-methyl-9a-homoerythromycin A of the general Formula I (compound Ia: S=1,4-dioxane).

FIG. 3 is a crystal packing diagram of a further orthorhombic isostructural pseudopolymorph of 9-deoxo-9a-aza-9a-methyl-9a-homoerythromycin A of the general Formula I (compound Ib: S=tert-butanol).

FIG. 4 is a crystal packing diagram of a further orthorhombic isostructural pseudopolymorph of 9-deoxo-9a-aza-9a-methyl-9a-homoerythromycin A of the general Formula I (compound Ic: S=methyl tert-butyl ether (MTBE)).

FIG. 5 is a crystal packing diagram of a further orthorhombic isostructural pseudopolymorph of 9-deoxo-9a-aza-9a-methyl-9a-homoerythromycin A of the general Formula I (compound Id: S=cyclohexane).

FIG. 6 is a powder diffractogram of amorphous 9-deoxo-9a-aza-9a-methyl-9a-homoerythromycin A prepared according to the process of Example 11.

FIG. 7 is a scanning electron microscopy (SEM) image of the surface of amorphous 9-deoxo-9a-aza-9a-methyl-9a-homoerythromycin A as prepared by the procedure described in Example 11.

FIG. 8 is a graph of the dissolution rates of (i) amorphous 9-deoxo-9a-aza-9a-methyl-9a-homoerithromycin A as prepared by the procedure described in Example 11, (ii) the new isostructural orthorhombic pseudopolymorph of 9-deoxo-9a-aza-9a-methyl-9a-homoerithromycin A of general formula I (Ic: S=MTBE) as prepared by the procedure in Example 3, and (iii) commercial 9-deoxo-9a-aza-9a-methyl-9a-homoerithromycin A dihydrate in a medium of pH 3 at 37° C.

FIG. 9 is a graph of the dissolution rates of (i) amorphous 9-deoxo-9a-aza-9a-methyl-9a-homoerithromycin A as prepared by the procedure described in Example 11, (ii) the new isostructural orthorhombic pseudopolymorph of 9-deoxo-9a-aza-9a-methyl-9a-homoerithromycin A of general formula I (Ic: S=MTBE) as prepared by the procedure in Example 3, and (iii) commercial 9-deoxo-9a-aza-9a-methyl-9a-homoerithromycin A dihydrate in a medium of pH 6 at 37° C.

DETAILED DESCRIPTION OF THE INVENTION

The term "substantially pure" as used herein with reference to amorphous 9-deoxo-9a-aza-9a-methyl-9a-homoerythromycin A denotes amorphous 9-deoxo-9a-aza-9a-methyl-9a-homoerythromycin A that is at least 90% pure. To be more specific, the phrase "at least 90% pure" refers to amorphous 9-deoxo-9a-aza-9a-methyl-9a-homoerythromycin A of the present invention containing no more than 10% of another compound, particularly not more than 10% of any compound or pseudopolymorph or some other crystal form of 9-deoxo-9a-aza-9a-methyl-9a-homoerythromycin A. Preferably, the "substantially pure" amorphous 9-deoxo-9a-aza-9a-methyl-9a-homoerythromycin A contains 5% or less of any compound or pseudopolymorph or any other crystal form of 9-deoxo-9a-aza-9a-methyl-9a-homoerythromycin A. More preferably, the "substantially pure" amorphous 9-deoxo-9a-aza-9a-methyl-9a-homoerythromycin A contains 3% or less of any compound or pseudopolymorph or any other crystal form of 9-deoxo-9a-aza-9a-methyl-9a-homoerythromycin A.

The term "substantially pure" as used herein with reference to the new orthorhombic isostructural pseudopolymorphs of general Formula I, denotes a new orthorhombic isostructural pseudopolymorph of the general Formula I that is at least 90% pure. To be more specific, the phrase "at least 90% pure" refers to new orthorhombic isostructural pseudopolymorph of the general Formula I of the present invention containing not more than 10% of some other compound, especially not more than 10% of some other pseudopolymorph or some other crystal form of 9-deoxo-9a-aza-9a-methyl-9a-homoerythromycin A. Preferably, the "substantially pure" orthorhombic isostructural pseudopolymorph of the general Formula I contains 5% or less of any compound or pseudopolymorph or any other crystal form of 9-deoxo-9a-aza-9a-methyl-9a-homoerythromycin A. More preferably, the "substantially pure" orthorhombic isostructural pseudopolymorph of the general Formula I contains 3% or less of any compound or pseudopolymorph or any other crystal form of 9-deoxo-9a-aza-9a-methyl-9a-homoerythromycin A.

In addition, as used herein, the term "9-deoxo-9a-aza-9a-methyl-9a-homoerythromycin A material" utilized in step (a) of the process for forming the substantially pure amorphous 9-deoxo-9a-aza-9a-methyl-9a-homoerythromycin A hereof, refers to any form of 9-deoxo-9a-aza-9a-methyl-9a-homoerythromycin A, including crude or purified 9-deoxo-9a-aza-9a-methyl-9a-homoerythromycin A or a solvate or hydrate thereof, in either crystalline (such as monoclinic or orthorhombic pseudopolymorphs) or amorphous form; or the "native solution" of 9-deoxo-9a-aza-9a-methyl-9a-homoerythromycin A formed during the last step of its syntheses (e.g. from 9-deoxo-9a-aza-9a-homoerythromycin A ("9a-DeMet"), as one of its last intermediates).

As used herein, the term "crude 9-deoxo-9a-aza-9a-methyl-9a-homoerythromycin A" is intended to include 9-deoxo-9a-aza-9a-methyl-9a-homoerythromycin A of any purity less than pharmaceutically acceptable purity, including 9-deoxo-9a-aza-9a-methyl-9a-homoerythromycin A obtained prior to final purification thereof.

As used herein, the term "native solutions of 9-deoxo-9a-aza-9a-methyl-9a-homoerythromycin A" refers to solutions of 9-deoxo-9a-aza-9a-methyl-9a-homoerythromycin A in water or any organic solvents, or admixtures thereof, utilized in the final step of preparing 9-deoxo-9a-aza-9a-methyl-9a-homoerythromycin A from its last intermediates (e.g. from 9a-DeMet), prior to isolation of crude 9-deoxo-9a-aza-9a-methyl-9a-homoerythromycin A.

9-Deoxo-9a-aza-9a-homoerythromycin A ("9a-DeMet") used as starting material in the presently claimed methods is also referred to in the art as 11-aza-10-deoxo-10-dihydroerythromycin A (10-dihydro-10-deoxo-11-azaerythromycin A) (U.S. Pat. No. 4,328,334; *J. Chem Res.* (M) 1988, 1239). It is known and obtainable e.g. by conventional methods (see: U.S. Pat. No. 4,328,334; *J. Chem. Soc., Perkin Trans. I* 1986, 1881).

Solvents utilized in the native solutions of 9-deoxo-9a-aza-9a-methyl-9a-homoerythromycin A may include water, chlorinated solvents, e.g. haloalkanes having one or two carbon atoms such as chloroform or dichloromethane; esters of acetic acid with a $C_2$–$C_4$ lower alkyl group such as ethyl acetate, isopropyl acetate or n-butyl acetate; monohydric $C_2$–$C_4$ alkanols such as isopropanol or 2-butanol; $C_1$–$C_4$ ketones such as acetone or isobutylketone; or aromatic or substituted aromatic solvents such as toluene.

1. Preparation of the Substantially Pure Amorphous 9-deoxo-9a-aza-Methyl-9a-Homoerythromycin A of the Invention Step (a)—Dissolving the 9-deoxo-9a-aza-9a-methyl-9a-homoerythromycin A Material As disclosed above, the 9-deoxo-9a-aza-9a-methyl-9a-homoerythromycin A material is dissolved in step (a) of the process for the preparation of the isostructural pseudopolymorphs of the invention in (1) an organic solvent which is water-miscible or water immiscible, (2) a mixture of such organic solvents, (3) a mixture of organic solvents and water or organic counter-solvent or (4) a mixture of organic solvent and water and at least one mineral or organic acid.

Suitable, but non-limiting, examples of organic solvents include linear or branched $C_5$–$C_{12}$ alkanes, such as pentane, hexane, heptane, octane, iso-octane, decane and dodecane; $C_5$–$C_8$ cycloalkanes, such as cyclopentane, cyclohexane, cycloheptane and cyclooctane; saturated or unsaturated linear or branched $C_1$–$C_6$ alkanols, such as methanol, ethanol, n-propanol, iso-propanol, n-butanol, iso-butanol, sec-butanol, tert-butanol, and allyl alcohol; $C_5$–$C_8$ cycloalkanols, such as cyclopentanol and cyclohexanol; arylalkanols, such as benzyl alcohol; saturated or unsaturated $C_2$–$C_4$ diols, such as 1,2-ethanediol, 1,2-propanediol, 1,3-propanediol, 1,4-butanediol and 2-butene-1,4-diol; triols such as glycerol; $C_1$–$C_6$ ethers, such as diethylether, monoglyme, diglyme, and 1,4-dioxane; $C_3$–$C_5$ ketones, such as acetone, and 2-butanone; $C_1$–$C_4$ alkyl esters of $C_1$–$C_4$ alkonoic- and hydroxy-alkanoic acids, such as methyl formate, ethyl formate, methyl acetate, ethyl acetate and ethyl lactate; amides, such as dimethylformamide and dimethylacetamide; ureas, such as N,N,N',N'-tetramethylurea; $C_2$–$C_4$ nitriles, such as acetonitrile and propionitrile; sulfoxides, such as dimethyl sulfoxide; sulfones, such as sulfolane; one or more heterocyclic amines, such as N-methylmorpholine; lactams, such as 2-pyrrolidone; N-methylpyrolidone or mixtures thereof; or their mixtures with water or some other organic counter-solvent such as linear or branched $C_5$–$C_{12}$ alkanes or cycloalkanes.

Suitable organic counter-solvents include, but are not limited to, linear or branched $C_5$–$C_{12}$ alkanes, such as pentane, hexane, heptane, octane, iso-octane, decane and dodecane; $C_5$–$C_8$ cycloalkanes, such as cyclopentane, cyclohexane, cycloheptane and cyclooctane.

Acids which may be utilized for the acidification employed in step (a) of the process of the present invention may comprise one or more of any common mineral or organic acids. Suitable examples include, but are not limited to, hydrochloric acid; sulfonic acid; sulfuric acid; sulfurous acid; phosphoric acid; carbonic acid; saturated or unsaturated $C_1$–$C_4$ unsubstituted or halo- or hydroxy-substituted alkanoic mono and di-carboxylic acids, such as formic acid, acetic acid, propionic acid, citric acid, tartaric acid, maleic acid, oxalic acid, and chloroacetic acid; arylalkanoic acids, such as benzoic acid; alkylsulfonic acids, such as methanesulfonic acid; aryl sulfonic acids, such as p-toluene sulfonic acid; and mixtures thereof.

The dissolution of the 9-dexo-9a-aza-9a-methyl-9a-homoerythromycin A material in step (a) is carried out generally at temperatures from about 30 to about 100° C., preferably at from about 30 to about 80° C., and more preferably at from about 40 to about 60° C. The volume of the solvent used is such that it suffices for dissolving the 9-deoxo-9-a-aza-9a-methyl-9a-homoerythromycin A charged therein.

Step (b)—Crystallization of Orthorhombic Pseudopolymorphs

The new orthorhombic pseudopolymorphs of 9-deoxo-9a-aza-9a-methyl-9a-homoerythromycin A useful as intermediates in the preparation of substantially pure amorphous 9-dexo-9a-aza-9a-methyl-9a-homoerythromycin A have the general Formula I:

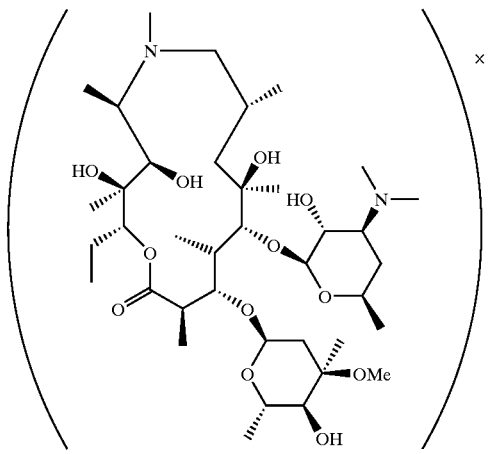

wherein S is a water-miscible or water-immiscible organic solvent;

the pseudopolymorphs being characterized by the orthorhombic space group $P2_12_12_1$, and average unit cell parameters of, crystal axis lengths from a=8.2 to 9.7 Å, b=11.5 to 13.5 Å, c=44.5 to 47.0 Å, and angles between the crystal axes of $\alpha=\beta=\gamma=90°$.

The new orthorhombic pseudopolymorphs of the invention are crystallized from the 9-deoxo-9a-aza-9a-methyl-9a-homoerythromycin A solution in step (b) of the process hereof by either controlled cooling, isothermal saturation of the solution with water until slight turbidity of the solution occurs, or by neutralization of the acidic solution with a common inorganic or organic base.

Inorganic bases which may be so utilized include common inorganic bases, such as the hydroxides, oxides or carbonates of Groups I or II of The Periodic Table Of The Elements, e.g., the alkali metal or alkaline earth metal bases such as lithium, sodium, potassium, barium, magnesium or calcium hydroxide; sodium, magnesium or calcium oxide; sodium or potassium carbonate; and also ammonia solutions. Organic bases which are so useful include organic amines, such as trimethylamine, triethylamine, piperidine, 3-methylpyridine, piperazine, triethanolamine or ethylene diamine; or quaternary organic hydroxides, such as tetramethyl-, tetraethyl- or tetrabutyl-ammonium hydroxide.

The crystallization may be carried out with or without crystal seeding i.e., by the addition of small amounts of the orthorhombic pseudopolymorphs of the present invention, in amounts of from about 0.01 to about 5.0% based on the amount of the initial 9-deoxo-9a-aza-9a-methyl-9a-homoerythromycin A material treated.

The crystallization, whether performed by controlled cooling, isothermal saturation or neutralization of the acidic solution with base, is carried out generally at temperatures of from about −10° C. to about 80° C., preferably at from about 0° C. to about 65° C., and most desirably at from about 25° C. to about 60° C. The crystallization is typically completed in a period of from about 30 minutes to about 7 days.

Step (c) Isolating the Orthorhombic Pseudopolymorphs

The crystalline orthorhombic pseudopolymorphs hereof may be isolated in step (c) in conventional manner, e.g., by centrifugation, filtration or the like, operating under reduced, atmospheric or elevated pressures. The isolated orthorhombic pseudopolymorphs are then washed in an organic solvent (such as those described at (1), (2) or (3) in step (a) hereinabove) or in such a solvent admixed with water. The resulting intermediate product is then dried in conventional manner, e.g., by fluid bed drying, operating under atmospheric pressure at temperatures of from about 20° to about 120° C., or under reduced pressures of from about 2 to about 80 kPa and at temperatures of from about 30° C. to about 120° C.

The orthorhombic isostructural pseudopolymorphs of 9-deoxo-9a-aza-9a-methyl-9a-homoerythromycin A of the general Formula I prepared according to the process of this invention comprise a stoichiometric ratio of 1:1:1, as defined by the general Formula I, of 9-deoxo-9a-aza-9a-methyl-9a-homoerythromycin A molecules: water: water-miscible or water-immiscible organic solvent (S). This is confirmed by X-ray crystal diffraction structures (see Table 1, and FIGS. 2 to 5). The crystallographic data shows that the new orthorhombic isostructural pseudopolymorphs are characterized by the orthorhombic space group $P2_12_12_1$, with average unit cell parameters being a=8.2 to 9.7 Å, b=11.5 to 13.5 Å, c=44.5 to 47.0 Å, $\alpha=\beta=\gamma=90°$, wherein a, b and c represent the crystal axes lengths and $\alpha$, $\beta$ and $\gamma$ represent the angles between the crystal axes. The isostructural nature of these orthorhombic pseudopolymorphs is confirmed by their very similar, practically identical, powder diffractograms.

In contrast to 9-deoxo-9a-aza-9a-methyl-9a-homoerythromycin A dihydrate, which also crystallizes in the orthorhombic space group $P2_12_12_1$ and which has canals in the crystal lattice containing water molecules (See FIG. 1 and Table 1), the orthorhombic isostructural pseudopolymorphs of 9-deoxo-9a-aza-9a-methyl-9a-homoerythromycin A of general Formula I of the present invention have cavities inside the crystal lattice, in which water molecules and solvent molecules are placed. The unit cells of the orthorhombic pseudopolymorphs of the general Formula I of the present invention have a crystal axis a, which is almost 50% shorter, and a crystal axis c, almost 3 times longer than the corresponding unit cell measurements of 9-deoxo-9a-aza-9a-methyl-9a-homoerythromycin A dihydrate.

Step (d)—Transforming the Orthorhombic Pseudopolymorphs to Stable Substantially Pure Amorphous 9-deoxo-9a-aza-9a-methyl-9a-homoerythromycin A Finally, transformation of the crystalline dried (or wet) orthorhombic pseudopolymorph of Formula I formed in step (b) to the substantially pure amorphous form may be carried out by removal of solvent and excess water by lyophilization, or by drying under reduced pressures of from about 0.01 to about 80 kPa or at atmospheric pressure and temperatures of from about 100° to about 120° C.

The substantially pure amorphous 9-deoxo-9a-aza-9a-methyl-9a-homoerythromycin A prepared in the step (d) according to the process of this invention is characterized by non-existence of isolated peaks in the powder diffractogram, a water content from 1.5 to 2.5%, and a granular habit (see, e.g., FIG. 7 which is a scanning electron microscopy (SEM) image of the amorphous 9-deoxo-9a-aza-9a-methyl-9a-homoerythromycin A prepared in Example 11).

The substantially pure amorphous 9-deoxo-9a-aza-9a-methyl-9a-homoerythromycin A prepared in step (d) according to the process of this invention is also characterized by a specific dissolution profile as well as a specific intrinsic dissolution rate (IDR), which substantially differ from the dissolution profile and the IDR of 9-deoxo-9a-aza-9a-methyl-9a-homoerythromycin A dihydrate measured under the same conditions.

The substantially pure amorphous 9-deoxo-9a-aza-9a-methyl-9a-homoerythromycin A prepared in the step (d) according to the present process is not hygroscopic and it is stable at normal storage conditions with regard to chemical stability as well as to the stability of the "crystal" form.

Substantially pure amorphous 9-deoxo-9a-aza-9a-methyl-9a-homoerythromycin A prepared by reproduction of the process of the present invention is obtained with the same yield and has identical characteristics, i.e. the process is robust and very well reproducible.

Formulations of the Substantially Pure Amorphous 9-deoxo-9a-aza-9a-Methyl-9a-Homoerythromycin A of the Present Invention and/or the Orthorhombic Isostructural Pseudopolymorphs of 9-deoxo-9a-aza-9a-methyl-9a-Homoerythromycin A The substantially pure amorphous 9-deoxo-9a-aza-9a-methyl-9a-homoerythromycin A prepared according to the present process and/or the orthorhombic isostructural pseudopolymorphs of 9-deoxo-9a-aza-9a-methyl-9a-homoerythromycin A, can be utilized in the preparation of rapid, controlled and also sustained release formulations, suitable for oral, rectal, parenteral, transdermal, buccal, nasal, sublingual, subcutaneous or intravenous administration such formulations may be useful for the treatment of bacterial and protozoan infections in humans and animals as well as other conditions such as inflammatory diseases.

The formulations are preferably administered orally, in the form of rapid or controlled release tablets, microparticles, mini tablets, capsules and oral solutions or suspensions, or powders for the preparation thereof. In addition to the new substantially pure amorphous 9-deoxo-9a-aza-9a-methyl-9a-homoerythromycin A of the present invention and/or the orthorhombic isostructural pseudopolymorphs of 9-deoxo-9a-aza-9a-methyl-9a-homoerythromycin A as the active substance, oral preparations may optionally include various standard pharmaceutical carriers and excipients, such as binders, fillers, buffers, lubricants, glidants, disintegrants, odorants, sweeteners, surfactants and coatings. Some excipients may have multiple roles in the formulations, e.g., act as both binders and disintegrants.

Examples of pharmaceutically acceptable disintegrants for oral formulations useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral formulations useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral formulations include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the formulations of the invention include, but are not limited to, magnesium stearate, talc, polyethylene glycol, polymers of ethylene oxide, sodium lauryl sulfate, magnesium lauryl sulfate, sodium oleate, sodium stearyl fumarate, DL-leucine and colloidal silicon dioxide Examples of suitable pharmaceutically acceptable odorants for the oral formulations include, but are not limited to, synthetic aromas and natural aromatic oils such as extracts of oils, flowers, fruits and combinations thereof. Preferable are vanilla and fruit aromas, including banana, apple, sour cherry, peach and similar aromas. Their use depends on many factors, the most important being the organoleptic acceptability for the population that will be taking the pharmaceutical formulations.

Examples of suitable pharmaceutically acceptable dyes for the oral formulations include, but are not limited to, synthetic and natural dyes such as titanium dioxide, beta-carotene and extracts of grapefruit peel.

Examples of useful pharmaceutically acceptable coatings for the oral formulations, typically used to facilitate swallowing, modify the release properties, improve the appearance, and/or mask the taste of the formulations include, but are not limited to, hydroxypropylmethylcellulose, hydroxypropylcellulose and acrylate-methacrylate copolymers.

Suitable examples of pharmaceutically acceptable sweeteners for the oral formulations include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Formulations of the substantially pure amorphous 9-deoxo-9a-aza-9a-methyl-9a-homoerythromycin A of the present invention and/or the orthorhombic isostructural pseudopolymorphs of 9-deoxo-9a-aza-9a-methyl-9a-homoerythromycin A can also be administered intravenously or intraperitoneally, by infusion or injection. Dispersions can also be prepared in a liquid carrier or intermediate, such as glycerin, liquid polyethylene glycols, triacetin oils, and mixtures thereof. To improve storage stability, such preparations may also contain a preservative to prevent the growth of microorganisms.

Pharmaceutical formulations suitable for injection or infusion may be in the form of a sterile aqueous solution, a dispersion or a sterile powder that contains the active ingredient, adjusted, if necessary, for preparation of such a sterile solution or dispersion suitable for infusion or injection. This may optionally be encapsulated into liposomes. In all cases, the final preparation must be sterile, liquid, and stable under production and storage conditions.

The liquid carrier or intermediate can be a solvent or liquid dispersive medium that contains, for example, water, ethanol, a polyol (e.g. glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants. Prevention of the action of micro-organisms can be achieved by the addition of various antibacterial and antifungal agents, e.g. paraben, chlorobutanol, or sorbic acid. In many cases isotonic substances are recommended, e.g. sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Sterile injectable solutions can be prepared by mixing the substantially pure 9-deoxo-9a-aza-9a-methyl-9a-homoerythromycin A and/or the orthorhombic isostructural pseudopolymorphs of 9-deoxo-9a-aza-9a-methyl-9a-homoerythromycin A with an appropriate solvent and one or more of the aforementioned excipients, followed by sterile filtering. In the case of sterile powders suitable for use in the preparation of sterile injectable solutions, preferable preparation methods include drying in vacuum and lyophilization, which provide powdery mixtures of the isostructural pseudopolymorphs and desired excipients for subsequent preparation of sterile solutions.

Due to the specific release properties, the substantially pure 9-deoxo-9a-aza-9a-methyl-9a-homoerythromycin A of the present invention and/or the orthorhombic isostructural pseudopolymorphs of 9-deoxo-9a-aza-9a-methyl-9a-homoerythromycin A may also be used for the preparation of locally acting, topical formulations. Such formulations may also contain other pharmaceutically acceptable excipients, such as polymers, oils, liquid carriers, surfactants, buffers, preservatives, stabilizers, antioxidants, moisturizers, emollients, colorants and odorants.

Examples of pharmaceutically acceptable polymers suitable for such topical formulations include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include but are not limited to, mineral oils, silicone oils, fatty acids, alcohols, and glycols.

Examples of suitable pharmaceutically acceptable liquid carriers include, but are not limited to, water, alcohols or glycols such as ethanol, isopropanol, propylene glycol, hexylene glycol, glycerol and polyethylene glycol, or mixtures thereof in which the substantially pure amorphous 9-deoxo-9a-aza-9a-methyl-9a-homoerythromycin A and/or the orthorhombic isostructural pseudopolymorphs of 9-deoxo-9a-aza-9a-methyl-9a-homoerythromycin A is dissolved or dispersed, optionally with the addition of non-toxic anionic, cationic or non-ionic surfactants, and inorganic or organic buffers.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyanisole.

Suitable examples of pharmaceutically acceptable moisturizers include, but are not limited to, glycerine, sorbitol, urea and polyethylene glycol.

Suitable examples of pharmaceutically acceptable emollients include, but are not limited to, mineral oils, isopropyl myristate, and isopropyl palmitate.

The use of dyes and odorants in topical formulations of the present invention depends on many factors of which the most important is organoleptic acceptability to the population that will be using the pharmaceutical formulations.

The therapeutically acceptable quantity of the substantially pure amorphous 9-deoxo-9a-aza-9a-methyl-9a-homoerythromycin A of the present invention and/or the orthorhombic isostructural pseudopolymorphs of 9-deoxo-9a-aza-9a-methyl-9a-homoerythromycin A administered varies, dependent on the selected compound, the mode of administration, treatment conditions, age and status of the patient or animal species, and is subject to the final decision of the physician, clinician or veterinary doctor monitoring the course of treatment.

Suitable oral and parenteral doses may vary within the range of from about 1 to about 200 mg per kg of body weight per day, preferably from about 5 to about 100 mg per kg of body weight and more preferably from about 5 to about 50 mg per kg of body weight per day. The substantially pure amorphous 9-deoxo-9a-aza-9a-methyl-9a-homoerythromycin A and/or the orthorhombic isostructural pseudopolymorphs of 9-deoxo-9a-aza-9a-methyl-9a-homoerythromycin A may be formulated in a single dosage form that contains from about 1 to about 3000 mg, preferably from about 100 to about 200 mg, and more desirably from about 150 to about 600 mg of the active substance per unit dose.

The substantially pure amorphous 9-deoxo-9a-aza-9a-methyl-9a-homoerythromycin A and/or the orthorhombic isostructural pseudopolymorphs of 9-deoxo-9a-aza-9a-methyl-9a-homoerythromycin A prepared according to the invention may be formulated in a unit dosage form, e.g. containing 1 to 3000 mg, usually 100 to 2000 mg or best 150 to 600 mg of the active substance per unit dosage form.

EXAMPLES

The amorphous and orthorhombic pseudopolymorphs of the present invention were prepared as described in Examples 1–17 below, utilizing 9-deoxo-9a-aza-9a-methyl-9a-homoerythromycin A in various purities and crystalline forms, including anhydrous, hydrated and solvated forms, as substrates initially used therein. The various 9-deoxo-9a-aza-9a-methyl-9a-homoerythromycin A materials so utilized were commercially available or prepared in the manner disclosed in the prior art, to the extent that the conditions therein could be ascertained. In the experiments reported in the examples, the contents of the respective 9-deoxo-9a-aza-9a-methyl-9a-homoerythromycin A products were analyzed by HPLC, and residual solvent contents were determined by GC. TGA and DSC measurements were performed on a Perkin-Elmer TGA-7 instrument. Diffraction experiments were performed on Bruker-Nonius FR591/KappaCCD single crystal X-ray diffractometer and Philips X'PertPRO powder X-ray diffractometer equipped with Anton Paar TTK-100 humidity camera used for non-ambient data collection. The crystal structures of the several orthorhombic pseudopolymorphs thus produced are indicated in Table 1.

Preparation of the Orthorhombic Pseudopolymorphs

Example 1

Preparation of the Orthorhombic Pseudopolymorph of Formula Ia (S=1,4-dioxane) (Method A)

Crude 9-deoxo-9a-aza-9a-methyl-9a-homoerythromycin A (10.0 g, having a water content of 5.7%) was dissolved in 20 ml dioxane at a temperature of 80° C. The solution was treated with actived carbon, filtered, and cooled to room temperature over a period of 3 hours. The precipitated crystals were allowed to stand at room temperature for another 15 hours. The crystals were isolated and dried at atmospheric pressure and room temperature to constant weight. The product was 3.8 g of a crystalline orthorhombic isostructural pseudopolymorph of Formula Ia in the form of a 1,4-dioxane solvate (S=1,4-dioxane). The water content (determined by KF titration), was 2.54% and the 1,4-dioxane content (determined by GC) was 10.5%. Upon single crystal X-ray diffraction analysis, the orthorhombic pseudopolymorph was characterized as identified in Table 1 and FIG. 2.

Example 2

Preparation of the Orthorhombic Pseudopolymorph of Formula Ib (S=tert-butanol) (Method A)

Crude 9-deoxo-9a-aza-9a-methyl-9a-homoerythromycin A (10.0 g, having a water content of 5.7%) was dissolved in 20 ml tert-butanol at a temperature of 60° C. The solution was treated with actived carbon, filtered, and cooled to room temperature over a period of 2 hours. The precipitated crystals were allowed to stand at room temperature for a further 15 hours. The crystals were isolated and dried at atmospheric pressure and room temperature to constant weight. The product was 10.0 g of a crystalline orthorhombic isostructural pseudopolymorph of Formula Ib (S=tert-butanol). The water content was 2.17%, and the tert-butanol content was 8.6%. Upon single x-ray diffraction analysis, the orthorhombic pseudopolymorph was characterized as identified in Table 1 & FIG. 3.

Example 3

Preparation of the Orthorhombic Pseudopolymorph of Formula Ic (S=Methyl tert-butyl ether) (Method A)

Crude 9-deoxo-9a-aza-9a-methyl-9a-homoerythromycin A (10.0 g, having a water content of 5.7%) was dissolved in 45 ml methyl tert-butyl ether (MTBE) at a temperature of 50° C. The solution was treated with actived carbon, filtered, and cooled to room temperature over a period of 2 hours. The precipitated crystals were allowed to stand at room temperature for a further 15 hours. The crystals were isolated and dried at atmospheric pressure and room temperature to constant weight. The product was 8.8 g of the orthorhombic isostructural pseudopolymorph of general Formula Ic (S=methyl tert-butyl ether). The water content was 2.4%, and the MTBE content was 7.9%. Upon single x-ray diffraction analysis, the orthorhombic pseudopolymorph was characterized as identified in Table 1 and FIG. 4.

Example 4

Preparation of the Orthorhombic Pseudopolymorph of Formula Id (S=cyclohexane) (Method A)

Crude 9-deoxo-9a-aza-9a-methyl-9a-homoerythromycin A (5.0 g, having a water content of 5.7%) was dissolved in 55 ml cyclohexane at a temperature of 70° C. The solution was treated with actived carbon, filtered, and cooled to room temperature over a period of 2 hours. The precipitated crystals were allowed to stand at room temperature for a further 15 hours. The crystals were isolated and dried at atmospheric pressure and room temperature to constant weight. The product was 4.7 g of the orthorhombic isostructural pseudopolymorph of Formula Id (S=cyclohexane). The water content was 2.35%, and the cyclohexane content was 7.9%. Upon single x-ray diffraction analysis, the orthorhombic pseudopolymorph was characterized as identified in Table 1 and FIG. 5.

Example 5

Preparation of Orthorhombic Pseudopolymorph of Formula Ia (S=1,4-dioxane) (Method B)

9-Deoxo-9a-aza-9a-homoerythromycin A (9a-DeMet) (1 mole), formic acid (1.8 to 2.5 mole/mole 9a-DeMet) and formalin (1 to 1.5 mole formaldehyde/mole 9a-DeMet) were added to 1,4-dioxane (4 to 8 l/kg 9a-DeMet). The mixture was heated to about 60° C. and stirred at this temperature for 4 hours. Whilst maintaining this temperature, activated carbon was added to the reaction mixture. The mixture was filtered, and the carbon remaining on the filter was washed with 1,4-dioxane (0.5 to 2 l/kg of the 9a-DeMet substrate). The combined 1,4-dioxane solution (both the filtrate and the wash) was then added to a previously prepared amount of water (10 to 20 l/kg 9a-DeMet) at temperature of about 25 to 30° C. The resulting mixture was alkalized stepwise with 10% NaOH solution to a pH 9.8, and then stirred at room temperature for 2 hours. The precipitate was a crystalline isostructural pseudopolymorph of the general Formula Ia (S=1,4-dioxane). The precipitate was filtered, washed with an aqueous 1,4-dioxane solution (10% v/v) and dried at room temperature under atmospheric pressure to constant weight. A minimum of 0.4 mole of the pseudopolymorph was thus prepared. The pseudopolymorph Ia obtained was analogous in form to that prepared in Example 1.

Example 6

Preparation of Orthohombic Pseudopolymorp of Formula Ib (S=tert-butanol) (Method B)

In an analogous manner to that set forth in Example 5, 9-deoxo-9a-aza-9a-homoerythromycin A was converted, using tert-butanol as a solvent at a crystallization temperature of 30° C. over a period of 70 hours, to a crystalline isostructural pseudopolymorph of the general formula Ib (S=tert-butanol). The product was filtered, washed with an aqueous solution of tert-butanol (5% v/v), and dried at a reduced pressure of 3 to 5 kPa and a temperature from 30 to 40° C. Yield: 0.7 mole. The pseudopolymorph Ib thus obtained was analogous to that prepared in Example 2.

Example 7

Preparation of Orthorhombic Isostructural Pseudopolymorph of Formula Id (S=cyclohexane) (Method C)

Amorphous 9-deoxo-9a-aza-9a-methyl-9a-homoerythromycin A (5.0 g, having a water content of 3.8%) was added to 55 ml cyclohexane. The mixture was heated to 40–50° C. with stirring. The solution was treated with activated carbon, filtered, and cooled to a temperature of 15° C. over a period of 2 hours. The mixture was seeded with the isostructural pseudopolymorph of 9-deoxo-9a-aza-9a-methyl-9a-homoerythromycin A of Formula Id (S=cyclohexane) and cooled stepwise to 0° C. with stirring over a 24 hour period. The precipitate thus formed was the crystalline isostructural pseudopolymorph Id in the form of the cyclohexane solvate (S=cyclohexane). The precipitate was filtered, washed with a minimum amount of cold cyclohexane and dried to constant weight at atmospheric pressure and room temperature. 4.7 g of the pseudopolymorph Id, analogous to that prepared in Example 4 was thus produced.

Example 8

Preparation of Orthorhombic Pseudopolymorph of the Formula Id (S=cyclohexane) (Method D)

Amorphous 9-deoxo-9a-aza-9a-methyl-9a-homoerythromycin A (5.0 g, having a water content of 3.8%) was dissolved in 55 ml cyclohexane with stirring at a temperature of 40° C. n-hexane was gradually added stepwise at this temperature, with stirring until slight turbidity formed. The solution was then gradually cooled to room temperature over 5 hours and allowed to stand at this temperature, without stirring, for a further 18 hours. The resulting precipitate was a crystalline orthorhombic isostructural pseudopolymorph of the Formula Id (S=cyclohexane). The precipitate was filtered, washed with a minimum amount of cold 10% v/v cyclohexane solution in n-hexane, and dried at atmospheric pressure and room temperature to constant weight. 4.9 g of the pseudopolymorph Id, analogous to that prepared in Example 4, was thus produced.

Example 9

Preparation of Pseudopolymorph of Formula Ic (S=methyl tert-butanol ether) (Method D)

9-Deoxo-9a-aza-9a-methyl-9a-homoerythromycin A dihydrate (5.0 g, purity: USP 25) was dissolved in 54 ml methyl tert-butyl ether. The stirred solution was heated to 30–40° C., and subsequently added gradually over a period of 2 hours to 70 ml hexane at 40° C., under seeding with 250 mg of the orthorhombic isostructural pseudopolymorph of the general Formula Ic (S=methyl tert-butyl ether). The mixture was then gradually cooled to −10° C. over 24 hours. The thus precipitated crystalline orthorhombic isostructural pseudopolymorph of the general formula Ic (S=methyl tert-butyl ether) was filtered, washed with a minimum amount of cold methyl tert-butyl ether, and dried at atmospheric pressure and room temperature to constant weight. 7.8 g of the pseudopolymorph Ic, analogous to that prepared in Example 3, was thus obtained.

Example 10

Preparation of Orthorhombic Pseudopolymorph of Formula Ia (S=1,4 dioxane) from a Native Solution of 9-deoxo-9a-aza-9a-methyl-9a-homoerythromycin A (Method E)

60 ml of a native solution of 9-deoxo-9a-aza-9a-methyl-9a-homoerythromycin A in ethyl acetate, prepared as described in WO 01/00640, was diluted with a further 40 ml of ethyl acetate. The resulting mixture was alkalized with 10% NaOH solution to a pH value of 9.8, and the layers separated. The ethyl acetate layer was washed with a saturated sodium chloride solution, and treated with activated carbon. The mixture was filtered and the carbon remaining on the filter was washed with 5 ml ethyl acetate. To the combined ethyl acetate solution (both the filtrate and wash) 10 ml 1,4-dioxane was added. The ethyl acetate was distilled out at atmospheric pressure. The residue after distillation was slowly cooled from 100° C. to 30° C. over a period of 5 hours. The resulting precipitate was a crystalline isostructural pseudopolymorph of the general Formula Ia (S=1,4-dioxane). The precipitate was filtered, washed with a minimum amount of cold aqueous 1,4-dioxane solution (10% v/v) and dried at atmospheric pressure and room temperature to constant weight. 1.9 g of the pseudopolymorph Ia, analogous to that prepared in Example 1, was obtained.

Examples 11 and 12

Preparation of Stable Amorphous 9-deoxo-9a-aza-9a-methyl-9a-homoerythromycin A, from the Pseudopolymorph Ic (S=methyl-tert-butyl ether)

Example 11

The orthorhombic pseudopolymorph of the general Formula Ic (S=methyl tert-butyl ether) obtained according to Example 3, was dried at a temperature of 80° C., under a reduced pressure of 2 kPa to constant weight. The yield of the stable amorphous 9-deoxo-9a-aza-9a-methyl-9a-homoerythromycin A thus obtained was quantitative; purity: according to USP 25. A powder diffractogram and scanning electron microscopy (SEM) image of the stable amorphous product thus obtained are set forth in FIGS. 6 and 7, respectively.

Example 12

In a similar manner to the procedure set forth in Examples 10 and 9, a crystalline isostructural pseudopolymorph of the general formula Ic (S=methyl tert-butyl ether) was obtained from a native dichloromethane solution of 9-deoxo-9a-aza-9a-methyl-9a-homoerythromycin A. The pseudopolymorph Ic was filtered, washed with cold methyl tert-butyl ether, and dried at a temperature between 70 and 80° C. under a reduced pressure of 2 to 5 kPa, to give amorphous 9-deoxo-9a-aza-9a-methyl-9a-homoerythromycin A. Yield: 0.6 mole; purity: USP 25. The product had a x-ray powder diffraction pattern identical to the product produced in Example 11.

Example 13

Preparation of Stable Amorphous 9-deoxo-9a-aza-9a-methyl-9a-homoerythromycin A, from the Pseudopolymorph Ia (S=1,4-dioxane)

The orthorhombic pseudopolymorph of Formula Ia (S=1, 4-dioxane) obtained according to Example 1, was dried at 50° C. and a reduced pressure of 0.1 kPa to constant weight. The yield and purity of the stable amorphous 9-deoxo-9a-aza-9a-methyl-9a-homoerythromycin A thus produced were identical to those of Example 11.

Example 14

Preparation of Stable Amorphous 9-deoxo-9a-aza-9a-methyl-9a-homoerythromycin A, from the Pseudopolymorph Ib (S=tert-butanol)

The orthorhombic pseudopolymorph of Formula Ib (S=tert-butanol) obtained according to Example 2, was dried at 80° C. under a reduced pressure of 13 Pa to constant weight. The yield and purity of the stable amorphous 9-deoxo-9a-aza-9a-methyl-9a-homoerythromycin A thus obtained were identical to those in Example 11.

Example 15

Preparation of Stable Amorphous 9-deoxo-9a-aza-9a-methyl-9a-homoerythromycin A, from the Pseudopolymorph Id (S=cyclohexane)

The orthorhombic pseudopolymorph of Formula Id (S=cyclohexane) obtained according to Example 4, was dried at 80° C. under a reduced pressure of 2 kPa to constant weight. The yield and purity of the stable amorphous 9-deoxo-9a-aza-9a-methyl-9a-homoerythromycin A thus obtained were identical to those of Example 11.

Example 16

Preparation of Stable Amorphous 9-deoxo-9a-aza-9a-methyl-9a-homoerythromycin A, from the Pseudopolymorph Ib (S=tert-butanol)

The orthorhombic pseudopolymorph of Formula Ib (S=tert-butanol), obtained according to Example 2, was sublimed at a temperature of 95° C. under a reduced pressure of 1 Pa to constant weight. The yield and purity of the stable amorphous 9-deoxo-9a-aza-9a-methyl-9a-homoerythromycin A thus obtained were identical to those of Example 11.

Example 17

Reprecipitation of Orthorhombic Pseudopolymorph of Formula Ia (S=1,4-dioxane)

5.0 g of the crystalline orthorhombic pseudopolymorph of Formula Ia (S=1,4-dioxane), obtained according to Example 1, was dissolved in 10 ml 1,4-dioxane at 50° C. To this 50° C. solution, water was added dropwise, with stirring, until slight turbidity occurred. The mixture was then cooled to room temperature over a period of 30 minutes and maintained at this temperature for a further 24 hours. The purified orthorhombic pseudopolymorph of Formula Ia (S=1,4-dioxane) thus formed was filtered, washed with a minimum amount of cold water and dried at 25° C. and atmospheric pressure to constant weight. 2.0 g of the purified pseudopolymorph of Formula Ia was thus obtained.

Example 18

Dissolution Profiles Of The New Isostructural Pseudopolymorph of 9-Deoxo-9a-aza-9a-methyl-9a-homoerythromycin of the General Formula I (Ia: S=MTBE) and the New Amorphous 9-Deoxo-9a-aza-9a-methyl-9a-homoerythromycin A Versus Commercial 9-deoxo-9a-aza-9a-methyl-9a-homoerythromycin A Dihydrate In order to compare the behaviour in vitro of the new isostructural orthorhombic pseudopolymorph of 9-deoxo-9a-aza-9a-methyl-9a-homoerythromycin A of the general formula I (Ic: S=MTBE) and the new amorphous 9-deoxo-9a-aza-9a-methyl-9a-homoerythromycin A of the invention with the commercial 9-deoxo-9a-aza-9a-methyl-9a-homoerythromycin A dihydrate, dissolution profiles have been determined at pH 3 and pH 6, at 37° C. For comparison, new pseudopolymorph Ic as prepared by the procedure in Example 3 above and new amorphous 9-deoxo-9a-aza-9a-methyl-9a-homoerythromycin A as prepared by the procedure in Example 11 above were used. The comparative dissolution profiles were determined by USP Method 2, PharmaTest Dissolution Tester, PTW SII; and the content of dissolved 9-deoxo-9a-aza-9a-methyl-9a-homoerythromycin A was measured by HPLC. The data thus obtained are set forth in Table 2 below, and plotted in FIGS. 8 (pH 3) and 9 (pH 6).

TABLE 2

Percent of Amorphous 9-deoxo-9a-aza-9a-methyl-9a-homoerythromycin A, Isostructural Pseudopolymorph of 9-deoxo-9a-aza-9a-methyl-9a-homoerythromycin A of General Formula I (Ic: S = MTBE) and Commercial 9-deoxo-9a-aza-9a-methyl-9a-homoerythromycin A Dihydrate Product Dissolved

| Time | Commercial 9-deoxo-9a-aza-9a-methyl-9a-homoerythromycin A Dihydrate | | Amorphous 9-deoxo-9a-aza-9a-methyl-9a-homoerythromycin A (Example 11) | | 9-Deoxo-9a-aza-9a-methyl-9a-homoerythromycin A Pseudopolymorph Ic (Example 3) | |
|---|---|---|---|---|---|---|
| Minutes | pH 3 | pH 6 | pH 3 | pH 6 | pH 3 | pH 6 |
| 5 | 3.9 | 14.5 | 14.3 | 78.5 | 12.3 | 74.0 |
| 10 | 8.1 | 27.3 | 26.5 | 97.5 | 29.4 | 98.8 |

TABLE 1

Crystallographic data for the orthorhombic isostructural pseudopolymorphs of the general Formula I of the invention (orthorhombic space group $P2_12_12_1$)

| Unit cell parameters | Ia (S = 1,4-dioxane) | Ib (S = tert-BuOH) | Ic (S = MTBE*) | Id (S = cyclohexane) | 9-Deoxo-9a-aza-9a-methyl-9a-homoerythromycin A dihydrate** |
|---|---|---|---|---|---|
| 295 K a/Å | 8.8290(20)[1] | | 8.92080(10) | 8.8573(23) | 17.860 |
| b/Å | 12.167(2) | | 12.34770(10) | 12.520(7) | 16.889 |
| c/Å | 45.853(8) | | 45.71900(10) | 45.624(11) | 14.752 |
| $\alpha = \beta = \gamma/°$ | 90 | | 90 | 90 | 90 |
| V/Å³ | 4925.64 | | 5036.01 | 5059.49 | 4449.76 |
| 100 K a/Å | | 8.84240(10) | 8.87150(10) | | |
| b/Å | | 11.91730(10) | 12.01090(10) | | |
| c/Å | | 45.9493(6) | 45.8956(4) | | |
| $\alpha = \beta = \gamma/°$ | | 90 | 90 | | |
| $\gamma/°$ | | | | | |
| V/Å³ | | 4842.02 | 4890.39 | | |

[1]Date in parentheses indicate the statistical variation of the last digit(s) of the reported parameter.
**Coded GEGJAD in Cambridge Crystollographic Database; Orthorhombic space group $P2_12_12_1$ TABLE 2-continued Percent of Amorphous 9-deoxo-9a-aza-9a-methyl-9a-homoerythromycin A, Isostructural Pseudopolymorph of 9-deoxo-9a-aza-9a-methyl-9a-homoerythromycin A of General Formula I (Ic: S = MTBE) and Commercial 9-deoxo-9a-aza-9a-methyl-9a-homoerythromycin A Dihydrate Product Dissolved

| Time Minutes | Commercial 9-deoxo-9a-aza-9a-methyl-9a-homoerythromycin A Dihydrate | | Amorphous 9-deoxo-9a-aza-9a-methyl-9a-homoerythromycin A (Example 11) | | 9-Deoxo-9a-aza-9a-methyl-9a-homoerythromycin A Pseudopolymorph Ic (Example 3) | |
|---|---|---|---|---|---|---|
| | pH 3 | pH 6 | pH 3 | pH 6 | pH 3 | pH 6 |
| 20 | 14.6 | 44.2 | 50.5 | 98.7 | 52.5 | 98.6 |
| 45 | 26.7 | 69.1 | 85.8 | 96.7 | 92.2 | 95.3 |
| 60 | 33.3 | 73.7 | 89.5 | 95.1 | 93.2 | 94.6 |

Example 19

The intrinsic dissolution rates (IDR) for the new amorphous 9-deoxo-9a-aza-9a-methyl-9a-homoerythromycin A prepared according to the procedure of Example 11, and the commercial 9-deoxo-9a-aza-9a-methyl-9a-homoerythromycin A dihydrate, in medium of pH 6 and 37° C., were determined by Intrinsic Dissolution Tester, Van Kel Type. The IDR for the new amorphous 9-deoxo-9a-aza-9a-methyl-9a-homoerythromycin A was about 2.79 mg min$^{-1}$ cm$^{-2}$, about 40% higher than the IDR of the prior art, i.e. 9-deoxo-9a-aza-9a-methyl-9a-homoerythromycin A dihydrate (about 1.8 mg min$^{-1}$cm$^{-2}$).

Example 20

Tablet Formulations

Amorphous 9-deoxo-9a-aza-9a-methyl-9a-homoerythromycin A formulations were prepared by granulating amorphous product (97%) with anhydrous calcium hydrogen phosphate, pregelatinized starch, lactose monohydrate, microcrystalline cellulose and croscarmellose sodium by standard granulation techniques. The dried granulates were homogenized with magnesium stearate and sodium lauryl sulphate and tabletted using standard tabletting machines. Tablet cores were coated with a HPMC based film coating containing hydroxypropylmethyl cellulose, titanium dioxide, polysorbate, talc and pigment. The quantities of ingredients for 250, 500 and 600 mg tablets are given in Table 3.

TABLE 3

TABLET FORMULATIONS OF AMORPHOUS 9-DEOXO-9A-AZA-9A-METHYL-9A-HOMOERYTHROMYCIN A

| Formulation Component/Dose: | 250 mg | 500 mg | 600 mg |
|---|---|---|---|
| Amorphous 9-deoxo-9a-aza-9a-methyl-9a-homoerythromycin A (97%) | 256 | 512 | 614 |
| Calcium hydrogen phosphate, anhydrous | 38 | 77 | 93 |
| Pregelatinized starch | 38 | 77 | 93 |
| Lactose monohydrate | 7 | 15 | 18 |
| Microcrystalline cellulose | 20 | 40 | 48 |
| Croscarmellose sodium | 4 | 8 | 9 |
| Sodium lauryl sulphate | 0.4 | 0.7 | 0.9 |
| Magneisum-stearate | 5 | 11 | 13 |
| HPMC (hydroxypropyl methylcellulose) | 13 | 26 | 31 |

Example 21

Topical Formulations

Water, co-solvents (glycerol, polyethylene glycol), preservatives (methyl and propylparaben), stabilizer and gelling polymer are homogenized by standard technique to form an aqueous phase.

The amorphous 9-deoxo-9a-aza-9a-methyl-9a-homoerythromycin A was added to such an aqueous phase and it was dispersed/dissolved. Oily components (such as liquid paraffin and cetyl alcohol), with the addition of emulsifier, were melted, and after being cooled, were mixed with the previously prepared aqueous phase. The final homogenisation was carried out under reduced pressure. Odorant may be added to the last phase, i.e. homogeneous gel, and optionally its pH may be adjusted. A typical amorphous 9-deoxo-9a-aza-9a-methyl-9a-homoerythromycin A containing formulation thus prepared is given in Table 4.

TABLE 4

Topical Formulation Containing Amorphous 9-Deoxo-9a-Aza-9a-Methyl-9a-Homoerythromycin A

| Component | Dose (mg/g) | Function |
|---|---|---|
| Amorphous 9-deoxo-9a-aza-9a-methyl-9a-homoerythromycin A | 100 | active substance |
| Glycerol | 100.00 | co-solvent |
| Isopropanol | 400.00 | co-solvent |
| PEG | 60.00 | co-solvent |
| Carbomer | 15.00 | gelling polymer |
| Citric acid | qs | pH adjustor |
| Polysorbate 40 | 10.00 | emulsifier |
| Methylparaben | 0.70 | preservative |
| Propylparaben | 0.30 | preservative |
| Disodium-EDTA | 0.5 | stabilizer |
| Liquid paraffin | 25.00 | oily component |
| Cetyl alcohol | 25.00 | oily component |
| Odorant | qs | |
| Water | up to 1 g | |

In these mixtures, a wide range of concentrations of the amorphous of 9-deoxo-9a-aza-9a-methyl-9a-homoerythromycin A can be utilized; a preservative may also be incorporated in the preparation depending on the dosage form (i.e., multidose or monodose).

All references, test methods, patents, and patent publications referred herein are incorporated by reference.

The present invention is not to be limited in scope by the specific embodiments herein. Various modifications of the invention, in addition to those described herein, will become apparent to those skilled in the art from the foregoing description. Such modifications are intended to fall within the scope of the appended claims.

What is claimed is:

1. A process for the preparation of a substantially pure amorphous 9-deoxo-9a-aza-9a-methyl-homoerythromycin A, wherein the procedure comprises the steps of:

a) dissolving 9-deoxo-9a-aza-9a-methyl-homoerythromycin A material in
      (1) an organic solvent that is water-miscible or water-immiscible,
      (2) a mixture of organic solvents,
      (3) a mixture of organic solvents and water, or
      (4) a mixture of water and at least one inorganic or organic acid;

b) crystallizing an orthorhombic isostructural pseudopolymorph of 9-deoxo-9a-aza-9a-methyl-9a-homoerythromycin A of the general Formula I:

I

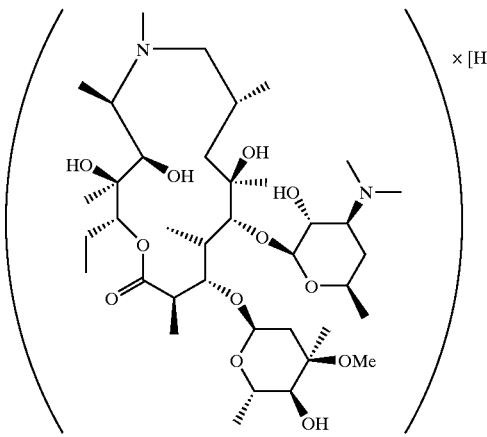

wherein S is a water-miscible or water-immiscible organic solvent, the pseudopolymorph being characterized by the orthorhombic space group $P2_12_12_1$ and average unit cell parameters comprising:

crystal axis lengths of a=8.2 to 9.7 Å, b=11.5 to 13.5 Å, and c=44.5 to 47.0 Å, and angles between the crystal axes of $\alpha=\beta=\gamma=90°$, from the solution thus prepared;

c) isolating the orthorhombic isostructural pseudopolymorph of the general Formula I; and d) converting the orthorhombic isostructural pseudopolymorph of 9-deoxo-9a-aza-9a-methyl-9a-homoerythromycin A of the general Formula I to a substantially pure amorphous 9-deoxo-9a-aza-9a-methyl-9a-homoerythromycin A.

2. The process of claim 1, wherein the 9-deoxo-9a-aza-9a-methyl-9a-homoerythromycin A material dissolved in step (a) is (i) a crystalline 9-deoxo-9a-aza-9a-methyl-9a-homoerythromycin A in crude or purified form, (ii) an amorphous 9-deoxo-9a-aza-9a-methyl-9a-homoerythromycin A in crude or purified form, (iii) solvates or hydrates of 9-deoxo-9a-aza-9a-methyl-9a-homoerythromycin A, whether in crude or purified form, or (iv) a native solution of 9-deoxo-9a-aza-9a-methyl-9a-homoerythromycin A formed during the last step of its syntheses from any one of its last intermediates.

3. The process of claim 2, wherein the 9-deoxo-9a-aza-9a-methyl-9a-homoerythromycin A utilized to prepare a substantially pure amorphous 9-deoxo-9a-aza-9a-methyl-9a-homoerythromycin A, dissolved in step (a) is a crude 9-deoxo-9a-aza-9a-methyl-9a-homoerythromycin A in any of its known forms and having a purity less than the pharmaceutically acceptable purity.

4. The process of claim 2, wherein the native solution of 9-deoxo-9a-aza-9a-methyl-9a-homoerythromycin A used for preparing a substantially pure amorphous 9-deoxo-9a-aza-9a-methyl-9a-homoerythromycin A, in the solvent dissolved in step (a) is a solution of 9-deoxo-9a-aza-9a-methyl-9a-homoerythromycin A formed in the native solvent during the last step of its syntheses from any one of its last intermediates.

5. The process of claim 2, wherein the native solution of 9-deoxo-9a-aza-9a-methyl-9a-homoerythromycin A used for preparing substantially pure amorphous 9-deoxo-9a-aza-9a-methyl-9a-homoerythromycin A dissolved in step (a) is a solution of 9-deoxo-9a-aza-9a-methyl-9a-homoerythromycin A, formed in the native solvent during the last step of its syntheses from 9-deoxo-9a-aza-9a-homoerythromycin A as its last intermediate.

6. The process of claim 2, wherein the 9-deoxo-9a-aza-9a-methyl-9a-homoerythromycin A dissolved in step (a) is in the form of a dispersion of 9-deoxo-9a-aza-9a-methyl-9a-homoerythromycin A and the 9-deoxo-9a-aza-9a-homoerythromycin A intermediate in a native solvent used in the last step of a synthesis of crude 9-deoxo-9a-aza-9a-methyl-9a-homoerythromycin A.

7. The process of claim 4, wherein the native solvent in the native solution is selected from the group consisting of haloalkanes having 1 or 2 carbon atoms, esters of acetic acid with a $C_2$–$C_4$ lower alkyl group, monohydroxyl $C_2$–$C_4$ alkanols, $C_1$–$C_4$ ketones, linear or cyclic ethers, aromatic or substituted aromatic compounds, and mixtures thereof.

8. The process of claim 2, wherein the 9-deoxo-9a-aza-9a-methyl-9a-homoerythromycin A dissolved in step (a) is amorphous 9-deoxo-9a-aza-9a-methyl-9a-homoerythromycin A; a crystalline anhydrous, monohydrate, dihydrate or solvate of 9-deoxo-9a-aza-9a-methyl-9a-homoerythromycin A; or an orthorhombic isostructural pseudopolymorph of 9-deoxo-9a-aza-9a-methyl-9a-homoerythromycin A of Formula I.

9. The process of claim 2, wherein the 9-deoxo-9a-aza-9a-methyl-9a-homoerythromycin A dissolved in step (a) is of pharmaceutically acceptable purity.

10. The process of claim 1, wherein step (a) is conducted at a temperature of from about 30° C. to about 100° C.

11. The process of claim 1, wherein the organic solvent in which the 9-deoxo-9a-aza-9a-methyl-9a-homoerythromycin A material is dissolved in step (a) is selected from the group consisting of linear or branched $C_1$–$C_5$ alkanes, $C_5$–$C_8$ cycloalkanes, linear or branched $C_1$–$C_6$ alkanols, $C_5$–$C_8$ cycloalkanols, arylalkanols, $C_2$–$C_4$ diols, triols, $C_1$–$C_4$ ethers, $C_3$–$C_5$ ketones, $C_1$–$C_4$ alkyl esters of $C_1$–$C_4$ alkanoic and hydroxyalkanoic acids, amides, ureas, $C_2$–$C_4$ nitriles, sulfoxides, sulfones, heterocyclic amines, lactams, and mixtures thereof.

12. The process of claim 1, wherein the inorganic of acid is selected from the group consisting of hydrochloric acid, sulfuric (VI) acid, sulfuric (IV) acid, and mixtures thereof.

13. The process of claim 1, wherein the organic acid is selected from the group consisting of formic acid, acetic acid, propionic acid, citric acid, tartaric acid, maleic acid, oxalic acid, chloroacetic acid, benzoic acid, methanesulfonic, p-toluenesulfonic acid, and mixtures thereof.

14. The process of claim 1, wherein the orthorhombic isostructural pseudopolymorph of 9-deoxo-9a-aza-9a-methyl-9a-homoerythromycin A is crystallized in step (b) by controlled cooling of the solution containing the 9-deoxo-9a-aza-9a-methyl-9a-homoerythromycin A at temperatures of from about 80° C. to about –10° C.

15. The process of claim 1, wherein the orthorhombic isostructural pseudopolymorph of 9-deoxo-9a-aza-9a-methyl-9a-homoerythromycin A is crystallized in step (b) isothermally at temperatures of from about 25° C. to about 60° C., by standing or mixing the solution formed in step (a) in a water-miscible or water-immiscible organic solvent at said isothermal conditions.

16. The process of claim 1, wherein the orthorhombic isostructural pseudopolymorph of 9-deoxo-9a-aza-9a-methyl-9a-homoerythromycin A is crystallized in step (b) isothermally at a temperature of about 25° C. to about 60° C. by saturating the solution formed in step (a) in a water-miscible or water-immiscible organic solvent with an organic counter-solvent until the solution becomes slightly turbid.

17. The process of claim 16, wherein the organic counter-solvent is water.

18. The process of claim 1, wherein the orthorhombic isostructural pseudopolymorph of 9-deoxo-9a-aza-9a- methyl-9a-homoerythromycin A is crystallized in step (b) by neutralizing the aqueous acidic solution of 9-deoxo-9a-aza-9a-methyl-9a-homoerythromycin A formed in step (a) at temperatures of about 80° C. to about −10° C.

19. The process of claim 1, wherein the orthorhombic isostructural pseudopolymorph of general Formula I is crystallized in step (b) by neutralizing an acidic solution of 9-deoxo-9a-aza-9a-methyl-9a-homoerythromycin A material from step (a) with one or more inorganic or organic base.

20. The process of claim 18, wherein the inorganic base is a alkali or alkali-earth metal hydroxide, oxide or carbonate, or an ammonia solution.

21. The process of claim 19, wherein the organic base is an organic amine.

22. The process of claim 21, wherein the organic amine is selected from the group consisting of trimethylamine, triethylamine, piperidine, 3-methylpyridine, piperazine, triethanolamine, and ethylene diamine.

23. The process of claim 19, wherein the organic base is a quaternary organic hydroxide.

24. The process of claim 23, wherein the quaternary organic hydroxide is selected from the group consisting of tetramethyl ammonium hydroxide, tetraethyl ammonium hydroxide, and tetrabutyl ammonium hydroxide.

25. The process according to claim 1, wherein the orthorhombic isostructural pseudopolymorph of 9-deoxo-9a-aza-9a-methyl-9a-homoerythromycin A of Formula I is added to the solution in step (b) in an amount of from about 0.01 to about 5.0 wt. % based on the amount of the starting 9-deoxo-9a-aza-9a-methyl-9a-homoerythromycin A, to seed crystallization of the orthorhombic isostructural pseudopolymorph of the general Formula I therein.

26. The process of claim 1, wherein the orthorhombic isostructural pseudopolymorph of 9-deoxo-9a-aza-9a-methyl-9a-homoerythromycin A of Formula I is isolated in step (c) by:
  (i) separating the pseudopolymorph from the solution formed in step (a);
  (ii) washing the obtained product with solvents (1), (2) or (3) used in step (a), at temperatures of from about −10° C. to about 40° C.; and
  (iii) drying the washed product under atmospheric pressure at temperatures of from about 20° C. to about 80° C., or under reduced pressures of from about 2 kPa to about 80 kPa.

27. The process of claim 1, wherein the orthorhombic isostructural pseudopolymorph of Formula I is transformed in step (d) to a substantially pure stable amorphous 9-deoxo-9a-aza-9a-methyl-9a-homoerythromycin A by lyophilizing or further drying the orthorhombic isostructural pseudopolymorph at reduced pressures from about 0.01 kPa to about 80 kPa and temperatures of from about −100° C. to about 100° C.

28. The process of claim 1, wherein the substantially pure amorphous 9-deoxo-9a-aza-9a-methyl-9a-homoerythromycin A prepared in step (d) is characterized by the non-existence of isolated peaks in powder diffractogram, by a water content of from bout 1.5 to about 2.5%, a granular habit, a specific dissolution profile as well as a specific intrinsic dissolution rate (IDR) at 37° C.

29. The substantially pure orthorhombic isostructural pseudopolymorph of Formula I, prepared by the process of claim 1.

30. A substantially pure orthorhombic isostructural pseudopolymorph of 9-deoxo-9a-aza-9a-methyl-9a-homoerythromycin A of the general formula I:

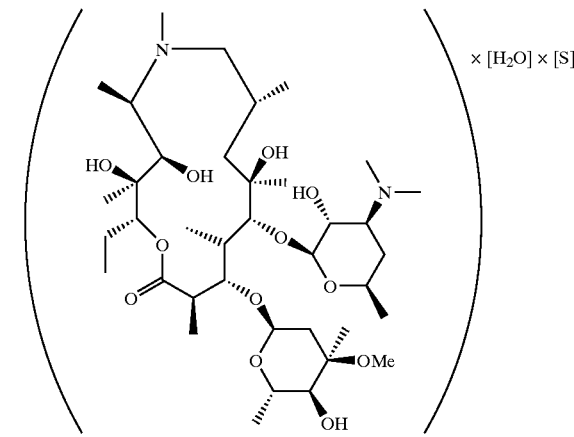

wherein S represents a water-miscible or water-immiscible organic solvent, characterized by the orthorhombic space group $P2_12_12_1$, and having average unit cell parameters of
  $a$=8.2 to 9.7 Å,
  $b$=11.5 to 13.5 Å,
  $c$=44.5 to 47.0 Å, $\alpha=\beta=\gamma=90°$,
wherein a, b and c represent the crystal axes lengths, and $\alpha$, $\beta$ and $\gamma$ represent the angles between the crystal axes.

31. The substantially pure orthorhombic isostructural pseudopolymorph of 9-deoxo-9a-aza-9a-methyl-9a-homoerythromycin A of claim 29 selected from the group of pseudopolymorphs (Ia)–(Id) set forth below, wherein S in Formula I and the average unit cell parameters, i.e. the crystal axes lengths a, b and c, and angles $\alpha$, $\beta$ and $\gamma$ between the crystal axes of the crystal structure are:
  (Ia) S=1,4-dioxane, and at 22° C.:
    $a$=8.8290(20) Å,
    $b$=12.167(2) Å,
    $c$=45.853(8) Å, and
    $\alpha=\beta=\gamma=90°$ C.,
  (Ib) S=tert-butanol and, at −173° C.:
    $a$=8.84240(10) Å,
    $b$=11.91730(10) Å,
    $c$=45.9493(6) Å, and
    $\alpha=\beta=\gamma=90°$ C.
  (Ic) S=methyl tert-butyl ether and, at 22° C.:
    $a$=8.92080(10) Å,
    $b$=12.34770(10) Å,
    $c$=45.71900(10) Å, and
    $\alpha=\beta=\gamma=90°$ C.,
  (Id) S=cyclohexane and, at 22° C.:
    $a$=8.8573(23) Å,
    $b$=12.520(7) Å,
    $c$=45.624(11) Å, and
    $\alpha=\beta=\gamma=90°$ C.

32. A pharmaceutical composition comprising substantially pure orthorhombic isostructural pseudopolymorph of 9-deoxo-9a-aza-9a-methyl-9a-homoerythromycin A according to claim 30, and one or more pharmaceutically acceptable excipients.

33. A method for treating bacterial and protozoal infections in humans and animals, comprising administering to a human or animal in need thereof the pharmaceutical composition of claim.

* * * * *